(12) United States Patent
Viksoe-Nielsen et al.

(10) Patent No.: US 7,998,709 B2
(45) Date of Patent: Aug. 16, 2011

(54) PROCESS OF PRODUCING A STARCH HYDROLYSATE

(75) Inventors: Anders Viksoe-Nielsen, Slangerup (DK); Carsten Andersen, Vaerlose (DK); Sven Pedersen, Gentofte (DK); Carsten Hjort, Vaerlose (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 12/540,472

(22) Filed: Aug. 13, 2009

(65) Prior Publication Data

US 2009/0305361 A1    Dec. 10, 2009

Related U.S. Application Data

(62) Division of application No. 10/877,007, filed on Jun. 25, 2004, now Pat. No. 7,618,795.

(60) Provisional application No. 60/482,589, filed on Jun. 25, 2003, provisional application No. 60/514,854, filed on Oct. 27, 2003.

(30) Foreign Application Priority Data

Jun. 25, 2003   (DK) ................................ 2003 00949
Oct. 24, 2003   (DK) ................................ 2003 01568

(51) Int. Cl.
| | |
|---|---|
| C12P 19/20 | (2006.01) |
| C12P 19/02 | (2006.01) |
| C12P 7/14 | (2006.01) |
| C12N 9/00 | (2006.01) |
| C12N 1/20 | (2006.01) |
| C12N 15/00 | (2006.01) |
| C07H 21/04 | (2006.01) |

(52) U.S. Cl. ..................... 435/96; 435/4; 435/6; 435/41; 435/69.1; 435/95; 435/105; 435/161; 435/162; 435/183; 435/200; 435/252.3; 435/320.1; 536/23.2

(58) Field of Classification Search ......................... None
See application file for complete search history.

(56) References Cited

U.S. PATENT DOCUMENTS

| | | | |
|---|---|---|---|
| 3,922,196 A | 11/1975 | Leach et al. | |
| 4,009,074 A | 2/1977 | Walon | |
| 4,235,965 A | 11/1980 | Walon | |
| 4,316,956 A | 2/1982 | Lutzen | |
| 4,474,883 A | 10/1984 | Yamamoto et al. | |
| 4,514,496 A | 4/1985 | Yoshizumi et al. | |
| 4,591,560 A | 5/1986 | Kainuma et al. | |
| 4,727,026 A | 2/1988 | Sawada et al. | |
| 6,054,302 A | 4/2000 | Shi et al. | |
| 2003/0013172 A1 | 1/2003 | Gerendash | |
| 2003/0125534 A1 | 7/2003 | Callen et al. | |
| 2003/0138786 A1 | 7/2003 | Callen et al. | |
| 2003/0170634 A1 | 9/2003 | Callen et al. | |
| 2004/0018607 A1 | 1/2004 | Callen et al. | |
| 2004/0219649 A1 | 11/2004 | Olsen et al. | |
| 2004/0234649 A1 | 11/2004 | Lewis et al. | |
| 2005/0042737 A1 | 2/2005 | Vikso-Nielsen et al. | |
| 2005/0176000 A1 | 8/2005 | Callen et al. | |
| 2006/0234280 A1 | 10/2006 | Callen et al. | |
| 2006/0294620 A1 | 12/2006 | Gray et al. | |
| 2007/0157329 A1 | 7/2007 | Callen et al. | |
| 2007/0161099 A1 | 7/2007 | Callen et al. | |

FOREIGN PATENT DOCUMENTS

| | | |
|---|---|---|
| EP | 0 140 410 | 5/1985 |
| EP | 0 171 218 | 2/1986 |
| JP | 58/005145 | 1/1983 |
| RU | 2085590 | 5/1995 |
| WO | WO 02/068589 | 9/2002 |
| WO | WO 03/066816 | 8/2003 |
| WO | WO 03/066826 | 8/2003 |
| WO | WO 03/068976 | 8/2003 |
| WO | WO 2005/092015 | 10/2005 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Iefuji et al, Biochem. J., vol. 318, pp. 989-996 (1996).
Lin et al., Database Small, Database Accession No. 059222 (XP002255839) (1996).
Itkor et al., Biochemical and Biophysical Research Communications, vol. 166, No. 2, pp. 630-636 (1990).
Itkor et al., Agr. Biol. Chem., vol. 53, No. 1, pp. 53-60 (1989).
Del-Rio et al., FEBS Letters, vol. 416, pp. 221-224 (1997).
Ueda et al., Microbiological Sciences, vol. 1, No. 1, pp. 21-24 (1984).
Ueda et al., Biotechnology and Bioengineering, vol. XXIII, pp. 291-299 (1981).
Hankyu Kyoei Bussan KK, Abstract of JP 57018991 (1982).
Haska et al., Starch/Starke, vol. 43, No. 3, pp. 102-107 (1991).
Hayashida et al., Applied and Environmental Microbiology, vol. 54, No. 6, pp. 1516-1522 (Jun. 1988).
Hayashida et al., Agric. Biol. Chem., vol. 46, No. 7, pp. 1947-1950 (1982).
Hayashida et al., Agric. Biol. Chem., vol. 39, vol. 11, pp. 2093-2099 (1975).
Hayashida et al., Agric. Biol. Chem., vol. 40, No. 1, pp. 141-146 (1976).
Hayashida et al., Agric. Biol. Chem., vol. 42, No. 5, pp. 927-933 (1978).
Hayashida et al., Agric. Biol. Chem., vol. 46, No. 6, pp. 1639-1645 (1982).
Hayashida et al., "The High Concentration Alcohol-Producing Factor in Koji", vol. 10, pp. 529-535 (1974).
Ueda et al., Die Starke, vol. 26, No. 11, pp. 374-378 (1974).
Labout et al., Starch/Starke, vol. 37, No. 5, pp. 157-161 (1985).
Jozo Shigen Kenkyusho KK, Abstract of JP 7099979 (1995).
Ueda et al., Die Starke, vol. 27, No. 4, pp. 123-128 (1975).

(Continued)

*Primary Examiner* — Christian Fronda
(74) *Attorney, Agent, or Firm* — Elias Lambiris

(57) ABSTRACT

The present invention relates to a process for enzymatic hydrolysis of granular starch into a soluble starch hydrolysate at a temperature below the initial gelatinization temperature of said granular starch.

31 Claims, No Drawings

OTHER PUBLICATIONS

Mikuni et al., Biotechnology and Bioengineering, vol., XXIX, pp. 729-732 (1987).
Norman et al., Cereal: A Renewable Resource, "Ethanol Process Considerations", pp. 651-665 (1981).
Su et al., Kor. J. Appl. Microbiol. Bioeng., vol. 14, No. 5, pp. 415-420 (1986).
Pranamuda et al., ISHS Acta Horticulturae 389: V International Sago Symposium, Abstract entitled "Ethanol Production from Raw Sago Starch Under Unsterile Condition", (Mar. 21, 2002).
Robertson et al., "Native or Raw Starch Digestion: A Key Step in Energy Efficient Biorefining of Grain", J. Agric. Food Chem., vol. 54, No. 2, pp. 353-365 (2006), web release Dec. 22, 2005.
Suresh et al., Bioprocess Engineering, vol. 21, pp. 165-168 (1999).
Yasmeen et al., Poster Presentation 6-23, "Ethanol Production from Raw Corn Starch by Saccharification with Glucoamylase from *Aspergillus niger* Mutant M 115 and Fermentation with *Saccharomyces cerevisiae*" (2004).
Richardson et al., J. Biol. Chem., vol. 277, Issue 29, pp. 26501-26507 (Jul. 19, 2002) (abstract only).
W.M. Ingledew, The Alcohol Textbook, Chapter 5, "Alcohol Production by *Saccharomyces cerevisiae*: A Yeast Primer", pp. 49-87 (1999).
Lin et al., Biotechnol. Appl. Biochem., vol. 28, pp. 61-68 (1998).
Singh et al., J. Basic Microbiol, vol. 35, No. 2, pp. 117-121 (1995) (Abstract only).
Fujio et al., Biotechnology and Bioengineering, vol. XXVII, pp. 1270-1273 (1985).
Shiau et al., Applied and Environmental Microbiology, vol. 69, No. 4, pp. 2383-2385 (Apr. 2003).
Saha et al., Biotechnology and Bioengineering, vol. XXV, pp. 1181-1186 (1983).
Fujio et al., Biotechnology and Bioengineering, Vol. XXVI, pp. 315-319 (1984).
Abe et al., Carbohydrate Research, vol. 175, pp. 85-92 (1988).
Kaneko et al., Journal of Fermentation and Bioengineering, vol. 81, No. 4, pp. 292-298 (1996).
Draft Protest Under 37 C.F.R. § 1.291 With Applicant's Consent Against U.S. Appl. No. 10/360,010 (2006).
Iefuji et al., Pub Med No. PMID: 8836148 (1996).
Saha et al., J. Ferment. Technol., vol. 61, No. 1, pp. 67-72 (1983).
MacGregor et al., Biochimica et Biophysica Acta, vol. 1546, pp. 1-20 (2001).
Haska et al., Starch/Starke, vol. 45, No. 7, pp. 241-244 (1993).
Hayashida et al., Agric. Biol Chem, vol. 45, No. 12, pp. 2675-2681 (1981).
Arasaratnam et al., Starch/Starke, vol. 50, No. 6, pp. 264-266 (1998).
Oh et al., Korean Journal Applied Microbiol Bioengineering, vol. 15, No. 6, pp. 408-413 (1987).
Park et al., Biotechnology and Bioengineering, Vol. XXIV, pp. 495-500 (1982).
Southall et al., FEBS Letters, vol. 447, pp. 58-60 (1999).
Janecek et al., Eur. J. Biochem, vol. 270, pp. 635-645 (2003).
Jorgensen et al., Biotechnology Letters, vol. 19, No. 10, pp. 1027-1031 (1997).
Chica et al., Current Opinion in Biotechnology, vol. 16, No. 4, pp. 378-384 (2005).
Witkowski et al., Biochemistry, vol. 38, No. 36, pp. 11643-11650 (1999).
Seffernick et al., Journal of Bacteriology, vol. 183, No. 8, pp. 2405-2410 (2001).

* cited by examiner

PROCESS OF PRODUCING A STARCH HYDROLYSATE

CROSS-REFERENCE TO RELATED APPLICATIONS

This application is a divisional of U.S. application Ser. No. 10/877,007 filed on Jun. 25, 2004 which claims priority or the benefit of Danish application nos. PA 2003 00949 and PA 2003 01568 filed Jun. 25, 2003 and Oct. 24, 2003, respectively, and U.S. Provisional application Nos. 60/482,589 and 60/514,854, filed Jun. 25, 2003 and Oct. 27, 2003, respectively, the contents of which are fully incorporated herein by reference.

CROSS-REFERENCE TO SEQUENCE LISTING

The present application contains a computer-readable form of a sequence listing, which is fully incorporated herein by reference.

FIELD OF THE INVENTION

The present invention relates to a process for hydrolysis of granular starch into a soluble starch hydrolysate at a temperature below the initial gelatinization temperature of said granular starch.

BACKGROUND OF THE INVENTION

A large number of processes have been described for converting starch to starch hydrolysates, such as maltose, glucose or specialty syrups, either for use as sweeteners or as precursors for other saccharides such as fructose. Glucose may also be fermented to ethanol or other fermentation products, such as citric acid, monosodium glutamate, gluconic acid, sodium gluconate, calcium gluconate, potassium gluconate, glucono delta lactone, sodium erythorbate, itaconic acid, lactic acid, gluconic acid; ketones; amino acids, glutamic acid (sodium monoglutaminate), penicillin, tetracyclin; enzymes; vitamins, such as riboflavin, B12, beta-carotene or hormones.

Starch is a high molecular-weight polymer consisting of chains of glucose units. It usually consists of about 80% amylopectin and 20% amylose. Amylopectin is a branched polysaccharide in which linear chains of alpha-1,4 D-glucose residues are joined by alpha-1,6 glucosidic linkages.

Amylose is a linear polysaccharide built up of D-glucopyranose units linked together by alpha-1,4 glucosidic linkages. In the case of converting starch into a soluble starch hydrolysate, the starch is depolymerized. The conventional depolymerization process consists of a gelatinization step and two consecutive process steps, namely a liquefaction process and a saccharification process.

Granular starch consists of microscopic granules, which are insoluble in water at room temperature. When an aqueous starch slurry is heated, the granules swell and eventually burst, dispersing the starch molecules into the solution. During this "gelatinization" process there is a dramatic increase in viscosity. As the solids level is 30-40% in a typical industrial process, the starch has to be thinned or "liquefied" so that it can be handled. This reduction in viscosity is today mostly obtained by enzymatic degradation. During the liquefaction step, the long-chained starch is degraded into smaller branched and linear units (maltodextrins) by an alpha-amylase. The liquefaction process is typically carried out at about 105-110° C. for about 5 to 10 minutes followed by about 1-2 hours at about 95° C. The temperature is then lowered to 60° C., a glucoamylase or a beta-amylase and optionally a debranching enzyme, such as an isoamylase or a pullulanase are added, and the saccharification process proceeds for about 24 to 72 hours.

It will be apparent from the above discussion that the conventional starch conversion process is very energy consuming due to the different requirements in terms of temperature during the various steps. It is thus desirable to be able to select the enzymes used in the process so that the overall process can be performed without having to gelatinize the starch. Such processes are the subject for U.S. Pat. Nos. 4,591,560, 4,727,026 and 4,009,074 and EP 0171218.

The present invention relates to a one-step process for converting granular starch into soluble starch hydrolysate at a temperature below initial gelatinization temperature of the starch.

SUMMARY OF THE INVENTION

In a first aspect the invention provides a process for producing a soluble starch hydrolysate, the process comprising subjecting a aqueous granular starch slurry at a temperature below the initial gelatinization temperature of said granular starch to the action of a first enzyme, which enzyme; is a member of the Glycoside Hydrolase Family 13; has alpha-1,4-glucosidic hydrolysis activity, and; comprises a functional Carbohydrate-Binding Module (CBM) belonging to CBM Family 20, which CBM has an amino acid sequence having at least 60% homology to an amino acid sequence selected from the group consisting of SEQ ID NO:1, SEQ ID NO:2, and SEQ ID NO:3; and which second enzyme is selected from the list comprising a fungal alpha-amylase (EC 3.2.1.1), a beta-amylase (E.C. 3.2.1.2), and a glucoamylase (E.C.3.2.1.3).

The process of the first aspect of the invention may be performed as a one step process and/or as a process comprising one or more steps.

In a second aspect the invention provides a process for production of high fructose starch-based syrup (HFSS), the process comprising producing a soluble starch hydrolysate by the process of the first aspect of the invention, and further comprising a step for conversion of the soluble starch hydrolysate into a high fructose starch-based syrup (HFSS).

In a third aspect the invention provides a process for production of fuel or potable ethanol; comprising producing a soluble starch hydrolysate by the process of the first aspect of the invention, and further comprising a step for fermentation of the soluble starch hydrolysate into ethanol, wherein the fermentation step is carried out simultaneously or separately/sequential to the hydrolysis of the granular starch.

In a fourth aspect the invention provides a use of an enzyme having alpha-amylase activity in a process for hydrolysis of starch, said enzyme comprising a functional CBM having an amino acid sequence having at least 60% homology to an amino acid sequence selected from the group consisting of SEQ ID NO:1, SEQ ID NO:2, and SEQ ID NO:3.

In a firth aspect the invention provides a use of an enzyme having alpha-amylase activity in a process for hydrolysis of granular starch, said enzyme comprising an amino acid sequence having at least 75%, least 80%, at least 85%, at least 90%, least 95%, at least 98%, such as at least 99% homology to an amino acid sequence selected from the group consisting of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, and SEQ ID NO:18.

In a sixth aspect the invention provides a use of an enzyme having alpha-amylase activity and a functional CBM in a process for hydrolysis of granular starch, said enzyme comprising an amino acid sequence having at least 75%, least 80%, at least 85%, at least 90%, least 95%, at least 98%, such as at least 99% homology to an amino acid sequence selected from the group consisting of SEQ ID NO:19, SEQ ID NO:20, SEQ ID NO:21 and SEQ ID NO:22.

DETAILED DESCRIPTION OF THE INVENTION

Definitions

The term "granular starch" is understood as raw uncooked starch, i.e., starch that has not been subjected to a gelatinization. Starch is formed in plants as tiny granules insoluble in water. These granules are preserved in starches at temperatures below the initial gelatinization temperature. When put in cold water, the grains may absorb a small amount of the liquid. Up to 50° C. to 70° C. the swelling is reversible, the degree of reversibility being dependent upon the particular starch. With higher temperatures an irreversible swelling called gelatinization begins.

The term "initial gelatinization temperature" is understood as the lowest temperature at which gelatinization of the starch commences. Starch heated in water begins to gelatinize between 50° C. and 75° C.; the exact temperature of gelatinization depends on the specific starch and can readily be determined by the skilled artisan. Thus, the initial gelatinization temperature may vary according to the plant species, to the particular variety of the plant species as well as with the growth conditions. In the context of this invention the initial gelatinization temperature of a given starch is the temperature at which birefringence is lost in 5% of the starch granules using the method described by Gorinstein and Lii, 1992, *Starch/Stärke* 44(12): 461-466.

The term "soluble starch hydrolysate" is understood as the soluble products of the processes of the invention and may comprise mono- di-, and oligosaccharides, such as glucose, maltose, maltodextrins, cyclodextrins and any mixture of these. Preferably at least 90%, 91%, 92%, 93%, 94%, 95%, 96%, 97% or 98% of the dry solids of the granular starch is converted into a soluble starch hydrolysate.

The term "Speciality Syrups", is an in the art recognised term and is characterised according to DE and carbohydrate spectrum (See the article "New Speciality Glucose Syrups", p. 50+, in the textbook "Molecular Structure and Function of Food Carbohydrate", Edited by G. G. Birch and L. F. Green, Applied Science Publishers LTD., London). Typically Speciality Syrups have a DE in the range from 35 to 45.

The "Glycoside Hydrolase Family 13" is in the context of this invention defined as the group of hydrolases comprising a catalytic module having a (beta/alpha)$_8$ or TIM barrel structure and acting on starch and related substrates through an alpha-retaining reacting mechanism (Koshland, 1953, *Biol. Rev. Camp. Philos. Soc.* 28: 416-436).

The enzymes having "alpha-1,4-glucosidic hydrolysis activity" is in the context of this invention defined as comprising the group of enzymes which catalyze the hydrolysis and/or synthesis of alpha-1,4-glucosidic bonds as defined by Takata (Takata et al, 1992, *J. Biol. Chem.* 267: 18447-18452) and by Koshland (Koshland, 1953, *Biol. Rev. Camp. Philos. Soc.* 28: 416-436).

The "Carbohydrate-Binding Module of Family 20" or a CBM-20 module is in the context of this invention defined as a sequence of approximately 100 amino acids having at least 45% homology to the Carbohydrate-Binding Module (CBM) of the polypeptide disclosed in FIG. 1 by Joergensen et al., 1997, *Biotechnol. Lett.* 19: 1027-1031. The CBM comprises the last 102 amino acids of the polypeptide, i.e., the subsequence from amino acid 582 to amino acid 683. The numbering of Glycoside Hydrolase Families applied in this disclosure follows the concept of Coutinho and Henrissat, 1999, *CAZy—Carbohydrate-Active Enzymes* server at URL: afmb.cnrs-mrs.fr/~cazy/CAZY/index.html or alternatively Coutinho, P. M. & Henrissat, B. 1999; The modular structure of cellulases and other carbohydrate-active enzymes: an integrated database approach. In "*Genetics, Biochemistry and Ecology of Cellulose Degradation*"., Ohmiya, Hayashi, Sakka, Kobayashi, Karita and Kimura eds., Uni Publishers Co., Tokyo, pp. 15-23, and Bourne and Henrissat, 2001, Glycoside hydrolases and glycosyltransferases: families and functional modules, *Current Opinion in Structural Biology* 11: 593-600.

A carbohydrate-binding module (CBM) is a polypeptide amino acid sequence which binds preferentially to a poly- or oligosaccharide (carbohydrate), frequently—but not necessarily exclusively—to a water-insoluble (including crystalline) form thereof.

Although a number of types of CBMs have been described in the patent and scientific literature, the majority thereof— many of which derive from cellulolytic enzymes (cellulases)—are commonly referred to as "cellulose-binding modules"; a typical cellulose-binding module will thus be a CBM which occurs in a cellulase. Likewise, other sub-classes of CBMs would embrace, e.g., chitin-binding modules (CBMs which typically occur in chitinases), xylan-binding modules (CBMs which typically occur in xylanases), mannan-binding modules (CBMs which typically occur in mannanases), starch-binding modules (CBMs which may occur in certain amylolytic enzymes, such as certain glucoamylases, or in enzymes such as cyclodextrin glucanotransferases), or in alpha-amylases.

CBMs are found as integral parts of large polypeptides or proteins consisting of two or more polypeptide amino acid sequence regions, especially in hydrolytic enzymes (hydrolases) which typically comprise a catalytic module containing the active site for substrate hydrolysis and a carbohydrate-binding module (CBM) for binding to the carbohydrate substrate in question. Such enzymes can comprise more than one catalytic module and one, two or three CBMs, and optionally further comprise one or more polypeptide amino acid sequence regions linking the CBM(s) with the catalytic module(s), a region of the latter type usually being denoted a "linker". Examples of hydrolytic enzymes comprising a CBM—some of which have already been mentioned above— are cellulases, xylanases, mannanases, arabinofuranosidases, acetylesterases and chitinases. CBMs have also been found in algae, e.g., in the red alga *Porphyra purpurea* in the form of a non-hydrolytic polysaccharide-binding protein.

In proteins/polypeptides in which CBMs occur (e.g., enzymes, typically hydrolytic enzymes), a CBM may be located at the N or C terminus or at an internal position.

That part of a polypeptide or protein (e.g., hydrolytic enzyme) which constitutes a CBM per se typically consists of more than about 30 and less than about 250 amino acid residues.

Preferred for the invention are enzymes comprising a CBM comprising an amino acid sequence selected from the group consisting of amino acid sequences SEQ ID NO:1, SEQ ID NO:2, and SEQ ID NO:3 as well as enzymes comprising a CBM comprising an amino acid sequence having at least 50% homology to an amino acid sequence selected from the group consisting of amino acid sequences SEQ ID NO:1, SEQ ID NO:2, and SEQ ID NO:3.

The polypeptide "homology" referred to in this disclosure is understood as the degree of identity between two sequences indicating a derivation of the first sequence from the second. The homology may suitably be determined by means of computer programs known in the art such as GAP provided in the GCG program package (Program Manual for the Wisconsin Package, Version 8, August 1994, Genetics Computer Group, 575 Science Drive, Madison, Wis., USA 53711) (Needleman and Wunsch, 1970, *Journal of Molecular Biology* 48: 443-453. The following settings for amino acid sequence comparison are used: GAP creation penalty of 3.0 and GAP extension penalty of 0.1.

The enzyme to be used as a first enzyme of the present invention is a four module alpha-amylase consisting of a three module amylase core and a separate carbohydrate binding module of family 20. The alpha-amylase may be a wild type alpha-amylase derived from bacterial or fungal sources, or it may be mutants, protein engineered variants, or other variants of such wild types, or it may be hybrids of variants or wild types.

Preferably the alpha-amylase is a wild type enzyme. More preferably the alpha-amylase is a variant and/or hybrid of the above alpha-amylases comprising amino acid modifications leading to increased activity, increased protein stability at low pH, and/or at high pH, increased stability towards calcium depletion, and/or increased stability at elevated temperature.

The term "Enzyme hybrids" referred to in this disclosure is understood as modified enzymes comprising an amino acid sequence of an amylolytic enzyme [which in the context of the present invention may, e.g., be an alpha-amylase (EC 3.2.1.1), an isoamylase (EC 3.2.1.68) or a pullulanase (EC 3.2.1.41)] linked (i.e., covalently bound) to an amino acid sequence comprising a CBM. The CBM is preferably but not exclusively fused to the N-terminal. The hybrid may comprise more than one CBM.

CBM-containing enzyme hybrids, as well as detailed descriptions of the preparation and purification thereof, are known in the art [see, e.g., WO 90/00609, WO 94/24158 and WO 95/16782, as well as Greenwood et al., 1994, *Biotechnology and Bioengineering* 44: 1295-1305]. They may, e.g., be prepared by transforming into a host cell a DNA construct comprising at least a fragment of DNA encoding the cellulose-binding module ligated, with or without a linker, to a DNA sequence encoding the enzyme of interest, and growing the transformed host cell to express the fused gene.

The construction of a hybrid protein between a carbohydrate binding module (CBM) and an alpha-amylase requires one or more of the following steps to obtain a stable, expressible and applicable enzyme.

1) Aligning the CBM-donor molecule with the donor of the catalytic modules using conventional methods is often required to identify possible crossing points. If the homology is relatively high there might be several possible crossing point. If however the homology is low or if only the sequence of the catalytic module and the CBM are available, respectively, the CBM can be attached as an elongation to the catalytic module either in the beginning of the sequence, i.e., in the N-terminal inserted after an eventually signal sequence; or in the C-terminal prior to the termination signal. Regardless if the CBM is located in the N- or in the C-terminal it might be beneficial to either delete a few amino acids or insert a number of amino acid as a linker to obtain an expressible and application stable enzyme.

2) Construction the DNA hybrid of the genes coding for the CBM and the amylolytic module according to the considerations made under 1) can be made by methods known to persons skilled in the art. These methods include among others, PCR reactions using primers designed to hybridize over the resulting DNA crossing point, DNA digesting followed by ligation or in-vivo combination for example by yeast.

3) A simple attachment of a CBM to an amylolytic module often results in a hybrid protein that is expressed poorly due to folding or stability problems or in a hybrid protein lacking sufficient stability and/or activity under a given application. To overcome such problems the hybrid protein may be subjected to protein engineering either by site directed mutagenesis methods or by more random approaches. This includes both the amino acids in the modules of the CBM and in the amylolytic modules as well as optimizing the transition from amylolytic module to CBM, with respect to length and amino acid sequence.

Preferred as a first enzyme for the present invention are hybrid enzymes comprising a CBM comprising an amino acid sequence selected from the group consisting of amino acid sequences SEQ ID NO:1, SEQ ID NO:2, and SEQ ID NO:3 as well as enzymes comprising an amino acid sequence having at least 50% at least 55%, at least 60%, at least 65%, at least 70%, at least 75%, least 80%, at least 85%, at least 90%, least 95%, at least 98%, such as at least 99% homology to an amino acid sequence selected from the group consisting of the amino acid sequences SEQ ID NO:1, SEQ ID NO:2, and SEQ ID NO:3.

Also preferred as a first enzyme for the present invention are hybrid enzymes comprising an amino acid sequence having alpha-amylolytic activity and comprising an amino acid sequence selected from the group consisting of amino acid sequences SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, and SEQ ID NO:18 as well as enzymes comprising an amino acid sequence having at least 70%, at least 75%, least 80%, at least 85%, at least 90%, least 95%, at least 98%, such as at least 99% homology to an amino acid sequence selected from the group consisting of amino acid sequences SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, and SEQ ID NO:18.

Preferably the first enzyme of the present invention comprises a CBM and/or an alpha-amylolytic sequence derived from a fungi, such as from a strain belonging to a *Talaromyces* sp., or from a strain belonging to an *Aspergillus* sp. such as *A. awamori, A. kawachii, A. niger, A. oryzae* etc. or from a bacteria, such as from a strain belonging to *Bacillus* sp, such as from a strain belonging to *B. amyloliquefacience, B. flavothermus, B. licheniformis* or *B. stearothermophilus*.

More preferred as a first enzyme of the present invention is a four module alpha-amylase consisting of a three module amylase core and a separate carbohydrate binding module of family 20. Most preferred is a four module alpha-amylase comprising an amino acid sequence having at least 70%, at least 75%, least 80%, at least 85%, at least 90%, least 95%, at least 98%, such as at least 99% homology to an amino acid sequence selected from the group consisting of SEQ ID NO:19, SEQ ID NO:20, SEQ ID NO:21 and SEQ ID NO:22.

Preferably the first enzyme of the present invention is a four module alpha-amylase isolated from a fungus or a bacteria, such as from a species of *Bacillus* sp, such as the polypeptides shown in SEQ ID NO:20 and SEQ ID NO:21, or from a strain of *Bacillus flavothermus*, such as the polypeptide shown in SEQ ID NO:19, or from a strain of *Aspergillus kawachii* such as the polypeptide shown in SEQ ID NO:22.

Most preferred as a first of the present invention is an alpha-amylase comprising an amino acid sequence having at least 70%, at least 75%, least 80%, at least 85%, at least 90%, least 95%, at least 98%, such as at least 99% homology to an amino acid sequence selected from the group consisting of SEQ ID NO:19, SEQ ID NO:20, SEQ ID NO:21 and SEQ ID NO:22.

The above alpha-amylases may be added in an amount of 0.001-1.0 KNU/g DS, preferably from 0.002-0.5 KNU/g DS, preferably 0.02-0.1 KNU/g DS.

Fungal Alpha-Amylase

A particular enzyme to be used as a second enzyme in the processes of the invention is a fungal alpha-amylase (EC 3.2.1.1), such as a fungamyl-like alpha-amylase. In the present disclosure, the term "fungamyl-like alpha-amylase" indicates an alpha-amylase which exhibits a high homology, i.e., more than 50%, 55%, 60%, 65%, 70%, 75%, 80%, 85% or even 90% homology to the amino acid sequence shown in SEQ ID No. 10 in WO96/23874. Fungal alpha-amylases may be added in an amount of 0.001-1.0 AFAU/g DS, preferably from 0.002-0.5 AFAU/g DS, preferably 0.02-0.1 AFAU/g DS.

Beta-Amylase

Another particular enzyme to be used as a second enzyme in the processes of the invention may be a beta-amylase (E.C 3.2.1.2). Beta-amylase is the name traditionally given to exo-acting maltogenic amylases, which catalyze the hydrolysis of 1,4-alpha-glucosidic linkages in amylose, amylopectin and related glucose polymers thereby releasing maltose.

Beta-amylases have been isolated from various plants and microorganisms (Fogarty and Kelly, 1979, *Progress in Industrial Microbiology* 15: 112-115). These beta-amylases are characterized by having optimum temperatures in the range from 40° C. to 65° C. and optimum pH in the range from 4.5 to 7.0. Contemplated beta-amylase include the beta-amylase from barley Spezyme® BBA 1500, Spezyme® DBA and Optimalt™ ME, Optimalt™ BBA from Genencor Int. as well as Novozym™ WBA from Novozymes A/S.

Glucoamylase

A further particular enzyme to be used as a second enzyme in the processes of the invention may also be a glucoamylase (E.C.3.2.1.3) derived from a microorganism or a plant. Preferred is glucoamylases of fungal or bacterial origin selected from the group consisting of *Aspergillus* glucoamylases, in particular *A. niger* G1 or G2 glucoamylase (Boel et al., 1984, *EMBO J.* 3(5): 1097-1102), or variants thereof, such as disclosed in WO 92/00381 and WO 00/04136; the *A. awamori* glucoamylase (WO 84/02921), *A. oryzae* (1991, *Agric. Biol. Chem.* 55(4): 941-949), or variants or fragments thereof.

Other contemplated *Aspergillus* glucoamylase variants include variants to enhance the thermal stability: G137A and G139A (Chen et al., 1996, *Prot. Engng.* 9: 499-505); D257E and D293E/Q (Chen et al., 1995, *Prot. Engng.* 8: 575-582); N182 (Chen et al., 1994, *Biochem. J.* 301: 275-281); disulphide bonds, A246C (Fierobe et al., 1996, *Biochemistry*, 35: 8698-8704; and introduction of Pro residues in position A435 and S436 (Li et al., 1997, *Protein Engng.* 10: 1199-1204. Other contemplated glucoamylases include *Talaromyces* glucoamylases, in particular derived from *Talaromyces emersonii* (WO 99/28448), *Talaromyces leycettanus* (U.S. Pat. No. Re.32,153), *Talaromyces duponti*, *Talaromyces thermophilus* (U.S. Pat. No. 4,587,215). Bacterial glucoamylases contemplated include glucoamylases from the genus *Clostridium*, in particular *C. thermoamylolyticum* (EP 135,138), and *C. thermohydrosulfuricum* (WO 86/01831). Preferred glucoamylases include the glucoamylases derived from *Aspergillus oryzae*, such as a glucoamylase having 50%, 55%, 60%, 65%, 70%, 75%, 80%, 85% or even 90% homology to the amino acid sequence shown in SEQ ID NO:2 in WO 00/04136. Also contemplated are the commercial products AMG 200L; AMG 300 L; SAN™ SUPER and AMG™ E (from Novozymes); OPTIDEX™ 300 (from Genencor Int.); AMIGASE™ and AMIGASE™ PLUS (from DSM); G-ZYME™ G900 (from Enzyme Bio-Systems); G-ZYME™ G990 ZR (*A. niger* glucoamylase and low protease content).

Glucoamylases may be added in an amount of 0.02-2.0 AGU/g DS, preferably 0.1-1.0 AGU/g DS, such as 0.2 AGU/g DS.

Additional Enzymes

The processes of the invention may be carried out in the presence of a third enzyme. A particular third enzyme may be a *Bacillus* alpha-amylase (often referred to as "Termamyl-like alpha-amylases"). Well-known Termamyl-like alpha-amylases include alpha-amylase derived from a strain of *B. licheniformis* (commercially available as Termamyl), *B. amyloliquefaciens*, and *B. stearothermophilus* alpha-amylase. Other Termamyl-like alpha-amylases include alpha-amylase derived from a strain of the *Bacillus* sp. NCIB 12289, NCIB 12512, NCIB 12513 or DSM 9375, all of which are described in detail in WO 95/26397, and the alpha-amylase described by Tsukamoto et al., 1988, *Biochemical and Biophysical Research Communications* 151: 25-31. In the context of the present invention a Termamyl-like alpha-amylase is an alpha-amylase as defined in WO 99/19467 on page 3, line 18 to page 6, line 27. Contemplated variants and hybrids are described in WO 96/23874, WO 97/41213, and WO 99/19467. Specifically contemplated is a recombinant *B. stearothermophilus* alpha-amylase variant with the mutations: I181*+G182*+N193F. *Bacillus* alpha-amylases may be added in effective amounts well known to the person skilled in the art.

Another particular third enzyme of the process may be a debranching enzyme, such as an isoamylase (E.C. 3.2.1.68) or a pullulanases (E.C. 3.2.1.41). Isoamylase hydrolyses alpha-1,6-D-glucosidic branch linkages in amylopectin and beta-limit dextrins and can be distinguished from pullulanases by the inability of isoamylase to attack pullulan, and by the limited action on alpha-limit dextrins. Debranching enzyme may be added in effective amounts well known to the person skilled in the art.

EMBODIMENTS OF THE INVENTION

The starch slurry to be subjected to the processes of the invention may have 20-55% dry solids granular starch, preferably 25-40% dry solids granular starch, more preferably 30-35% dry solids granular starch.

After being subjected to the process of the first aspect of the invention at least 85%, at least 86%, at least 87%, at least 88%, at least 89%, at least 90%, at least 91%, at least 92%, at least 93%, at least 94%, at least 95%, at least 96%, at least 97%, at least 98%, or preferably at least 99% of the dry solids of the granular starch is converted into a soluble starch hydrolysate.

According to the invention the processes of the first and second aspect is conducted at a temperature below the initial gelatinization temperature. Preferably the temperature at which the processes are conducted is at least 30° C., at least 31° C., at least 32° C., at least 33° C., at least 34° C., at least 35° C., at least 36° C., at least 37° C., at least 38° C., at least 39° C., at least 40° C., at least 41° C., at least 42° C., at least 43° C., at least 44° C., at least 45° C., at least 46° C., at least 47° C., at least 48° C., at least 49° C., at least 50° C., at least 51° C., at least 52° C., at least 53° C., at least 54° C., at least 55° C., at least 56° C., at least 57° C., at least 58° C., at least 59° C., or preferably at least 60° C.

The pH at which the process of the first aspect of the invention is conducted may in be in the range of 3.0 to 7.0, preferably from 3.5 to 6.0, or more preferably from 4.0-5.0.

The exact composition of the products of the process of the first aspect of the invention, the soluble starch hydrolysate, depends on the combination of enzymes applied as well as the type of granular starch processed. Preferably the soluble hydrolysate is maltose with a purity of at least 85%, at least 90%, at least 95.0%, at least 95.5%, at least 96.0%, at least 96.5%, at least 97.0%, at least 97.5%, at least 98.0%, at least 98.5, at least 99.0% or at least 99.5%. Even more preferably the soluble starch hydrolysate is glucose, and most preferably the starch hydrolysate has a DX (glucose percent of total solubilised dry solids) of at least 94.5%, at least 95.0%, at least 95.5%, at least 96.0%, at least 96.5%, at least 97.0%, at least 97.5%, at least 98.0%, at least 98.5, at least 99.0% or at least 99.5%. Equally contemplated, however, is the process wherein the product of the process of the invention, the soluble starch hydrolysate, is a speciality syrup, such as a speciality syrup containing a mixture of glucose, maltose, DP3 and DPn for use in the manufacture of ice creams, cakes, candies, canned fruit.

The granular starch to be processed in the processes of the invention may in particular be obtained from tubers, roots, stems, legumes, cereals or whole grain. More specifically the granular starch may be obtained from corns, corn grits, cobs, wheat, barley, rye, milo, sago, cassava, tapioca, sorghum, rice, peas, bean, banana or potatoes. Specially contemplated are both waxy and non-waxy types of corn and barley. The granular starch to be processed may be a highly refined starch quality, preferably at least 90%, at least 95%, at least 97% or at least 99.5% pure or it may be a more crude starch containing material comprising milled whole grain including non-starch fractions such as germ residues and fibres. The raw material, such as whole grain, is milled in order to open up the structure and allowing for further processing. Two milling processes are preferred according to the invention: wet and dry milling. In dry milling the whole kernel is milled and used. Wet milling gives a good separation of germ and meal (starch granules and protein) and is with a few exceptions applied at locations where the starch hydrolysate is used in production of syrups. Both dry and wet milling are well known in the art of starch processing and are equally contemplated for the processes of the invention. The process of the first aspect of the invention may be conducted in an ultrafiltration system where the retentate is held under recirculation in presence of enzymes, raw starch and water and where the permeate is the soluble starch hydrolysate. Equally contemplated is the process conducted in a continuous membrane reactor with ultrafiltration membranes and where the retentate is held under recirculation in presence of enzymes, raw starch and water and where the permeate is the soluble starch hydrolysate. Also contemplated is the process conducted in a continuous membrane reactor with microfiltration membranes and where the retentate is held under recirculation in presence of enzymes, raw starch and water and where the permeate is the soluble starch hydrolysate.

In the process of the second aspect of the invention the soluble starch hydrolysate of the process of the first aspect of the invention is subjected to conversion into high fructose starch-based syrup (HFSS), such as high fructose corn syrup (HFCS). This conversion is preferably achieved using a glucose isomerase, and more preferably by an immobilized glucose isomerase supported on a solid support. Contemplated isomerases comprises the commercial products Sweetzyme™ IT from Novozymes A/S, G-zyme™ IMGI and G-zyme™ G993, Ketomax™ and G-zyme™ G993 from Rhodia, G-zyme™ G993 liquid and GenSweet™ IGI from Genencor Int.

In the process of the third aspect of the invention the soluble starch hydrolysate of the process of the first aspect of the invention is used for production of fuel or potable ethanol. In the process of the third aspect the fermentation may be carried out simultaneously or separately/sequential to the hydrolysis of the granular starch slurry. When the fermentation is performed simultaneous to the hydrolysis the temperature is preferably between 30° C. and 35° C., and more preferably between 31° C. and 34° C. The process of the third aspect of the invention may be conducted in an ultrafiltration system where the retentate is held under recirculation in presence of enzymes, raw starch, yeast, yeast nutrients and water and where the permeate is an ethanol containing liquid. Equally contemplated is the process conducted in a continuous membrane reactor with ultrafiltration membranes and where the retentate is held under recirculation in presence of enzymes, raw starch, yeast, yeast nutrients and water and where the permeate is an ethanol containing liquid.

The soluble starch hydrolysate of the process of the first aspect of the invention may also be used for production of a fermentation product comprising fermenting the treated starch into a fermentation product, such as citric acid, monosodium glutamate, gluconic acid, sodium gluconate, calcium gluconate, potassium gluconate, glucono delta lactone, or sodium erythorbate.

In another embodiment the starch slurry is being contacted with a polypeptide comprising a CBM, but no amylolytic module, i.e., application of loose CBMs. The loose CBMs may be starch binding modules, cellulose-binding modules, chitin-binding modules, xylan-binding modules, mannan-binding modules, and other binding modules. Preferred CBMs in the present context are microbial CBMs, particularly bacterial or fungal CBMs. Particularly preferred are the starch binding modules shown in the present disclosure as the polypeptide sequences SEQ ID NO:1, SEQ ID NO:2, and SEQ ID NO:3 or the starch binding modules disclosed in U.S. provisional application No. 60/511,044 as SEQ ID NO:12; the CBM of the glucoamylase from *Hormoconis* sp. such as from *Hormoconis resinae* (Syn. Creosote fungus or *Amorphotheca resinae*) (SWISSPROT:Q03045), SEQ ID NO:13; the CBM from *Lentinula* sp. such as from *Lentinula edodes* (shiitake mushroom) (SPTREMBL:Q9P4C5), SEQ ID NO:14; the CBM from *Neurospora* sp. such as from *Neurospora crassa* (SWISSPROT:P14804), SEQ ID NO:15; the CBM from *Talaromyces* sp. such as from *Talaromyces byssochlamydioides*, SEQ ID NO:16; the CBM from *Geosmithia* sp. such as from *Geosmithia cylindrospora*, SEQ ID NO:17: the CBM from *Scorias* sp. such as from *Scorias spongiosa*, SEQ ID NO:18; the CBM from *Eupenicillium* sp. such as from *Eupenicillium ludwigii*, SEQ ID NO:19; the CBM from *Aspergillus* sp. such as from *Aspergillus japonicus*, SEQ ID NO:20; the CBM from *Penicillium* sp. such as from *Penicillium* cf. *miczynskii*, SEQ ID NO:21; the CBM from Mz1 *Penicillium* sp., SEQ ID NO:22; the CBM from *Thysanophora* sp., SEQ ID NO:23; the CBM from *Humicola* sp. such as from *Humicola grisea* var. *thermoidea*. Most preferred CBMs include the CBMs disclosed in U.S. provisional application No. 60/511,044 as SEQ ID NO:24; the CBM of the glucoamylase from *Aspergillus* sp. such as from *Aspergillus niger*, and as SEQ ID NO:25; the CBM of the glucoamylase from *Athelia* sp. such as from *Athelia rolfsii*. Also preferred for the invention is the application of any CBM having at least 50%, 60%, 70%, 80% or even at least 90% homology to any of the afore mentioned CBM amino acid sequences.

The loose CBMs may be applied to the granular starch slurry in effective amounts.

Materials and Methods

Alpha-Amylase Activity (KNU)

The amylolytic activity may be determined using potato starch as substrate. This method is based on the break-down of modified potato starch by the enzyme, and the reaction is followed by mixing samples of the starch/enzyme solution with an iodine solution. Initially, a blackish-blue colour is formed, but during the break-down of the starch the blue colour gets weaker and gradually turns into a reddish-brown, which is compared to a coloured glass standard.

One Kilo Novo alpha amylase Unit (KNU) is defined as the amount of enzyme which, under standard conditions (i.e., at 37° C.+/−0.05; 0.0003 M $Ca^{2+}$; and pH 5.6) dextrinizes 5.26 g starch dry substance Merck Amylum solubile.

A folder AF 9/6 describing this analytical method in more detail is available upon request to Novozymes A/S, Denmark, which folder is hereby included by reference.

Glucoamylase Activity (AGU)

The Novo Glucoamylase Unit (AGU) is defined as the amount of enzyme, which hydrolyzes 1 micromole maltose per minute at 37° C. and pH 4.3.

The activity is determined as AGU/ml by a method modified after (AEL-SM-0131, available on request from Novozymes) using the Glucose GOD-Perid kit from Boehringer Mannheim, 124036. Standard: AMG-standard, batch 7-1195, 195 AGU/ml. 375 microL substrate (1% maltose in 50 mM Sodium acetate, pH 4.3) is incubated 5 minutes at 37° C. 25 microL enzyme diluted in sodium acetate is added. The reaction is stopped after 10 minutes by adding 100 microL 0.25 M NaOH. 20 microL is transferred to a 96 well microtitre plate and 200 microL GOD-Perid solution (124036, Boehringer Mannheim) is added. After 30 minutes at room temperature, the absorbance is measured at 650 nm and the activity calculated in AGU/ml from the AMG-standard. A folder (AEL-SM-0131) describing this analytical method in more detail is available on request from Novozymes A/S, Denmark, which folder is hereby included by reference.

Fungal Alpha-Amylase Activity (FAU)

Fungal alpha-amylase activity may be measured in FAU (Fungal Alpha-Amylase Units). One (1) FAU is the amount of enzyme which under standard conditions (i.e., at 37° C. and pH 4.7) breaks down 5260 mg solid starch (Amylum solubile, Merck) per hour. A folder AF 9.1/3, describing this FAU assay in more details, is available upon request from Novozymes A/S, Denmark, which folder is hereby included by reference.

Acid Alpha-Amylase Activity (AFAU)

Acid alpha-amylase activity may be measured in AFAU (Acid Fungal Alpha-amylase Units), which are determined relative to an enzyme standard.

The standard used is AMG 300 L (from Novozymes A/S, glucoamylase wild-type *Aspergillus niger* G1, also disclosed in Boel et al., 1984, *EMBO J* 3(5): 1097-1102 and in WO 92/00381). The neutral alpha-amylase in this AMG falls after storage at room temperature for 3 weeks from approx. 1 FAU/mL to below 0.05 FAU/mL.

The acid alpha-amylase activity in this AMG standard is determined in accordance with the following description. In this method 1 AFAU is defined as the amount of enzyme, which degrades 5.26 mg starch dry solids per hour under standard conditions.

Iodine forms a blue complex with starch but not with its degradation products. The intensity of colour is therefore directly proportional to the concentration of starch. Amylase activity is determined using reverse colorimetry as a reduction in the concentration of starch under specified analytic conditions.

$$\text{Starch} + \text{Iodine} \xrightarrow[t = 23 \text{ sec.}]{\text{Alpha-amylase} \atop 40° \text{C., pH 2.5}} \text{Dextrins} + \text{Oligosaccharides}$$

Blue/violet → Decoloration

| Standard conditions/reaction conditions: (per minute) | |
|---|---|
| Substrate: | starch, approx. 0.17 g/L |
| Buffer: | Citate, approx. 0.03 M |
| Iodine (I2): | 0.03 g/L |
| $CaCl_2$: | 1.85 mM |
| pH: | 2.50-0.05 |
| Incubation temperature: | 40° C. |
| Reaction time: | 23 seconds |
| Wavelength: | lambda = 590 nm |
| Enzyme concentration: | 0.025 AFAU/mL |
| Enzyme working range: | 0.01-0.04 AFAU/mL |

If further details are preferred these can be found in EB-SM-0259.02/01 available on request from Novozymes A/S, and incorporated by reference.

Beta-Amylase Activity (DP°)

The activity of SPEZYME® BBA 1500 is expressed in Degree of Diastatic Power (DP°). It is the amount of enzyme contained in 0.1 ml of a 5% solution of the sample enzyme preparation that will produce sufficient reducing sugars to reduce 5 ml of Fehling's solution when the sample is incubated with 100 ml of substrate for 1 hour at 20° C.

Pullulanase Activity (New Pullulanase Unit Novo (NPUN))

Pullulanase activity may be determined relative to a pullulan substrate. Pullulan is a linear D-glucose polymer consisting essentially of maltotriosyl units joined by 1,6-alpha-links. Endo-pullulanases hydrolyze the 1,6-alpha-links at random, releasing maltotriose, $6^3$-alpha-maltotriosyl-maltotriose, $6^3$-alpha-($6^3$-alpha-maltotriosyl-maltotriosyl)-maltotriose.

One new Pullulanase Unit Novo (NPUN) is a unit of endo-pullulanase activity and is measured relative to a Novozymes A/S Promozyme D standard. Standard conditions are 30 minutes reaction time at 40° C. and pH 4.5; and with 0.7% pullulan as substrate. The amount of red substrate degradation product is measured spectrophotometrically at 510 nm and is proportional to the endo-pullulanase activity in the sample. A folder (EB-SM.0420.02/01) describing this analytical method in more detail is available upon request to Novozymes A/S, Denmark, which folder is hereby included by reference.

Under the standard conditions one NPUN is approximately equal to the amount of enzyme which liberates reducing carbohydrate with a reducing power equivalent to 2.86 micromole glucose per minute.

Determination of Sugar Profile and Solubilised Dry Solids

The sugar composition of the starch hydrolysates was determined by HPLC and glucose yield was subsequently calculated as DX. °BRIX, solubilised (soluble) dry solids of the starch hydrolysate were determined by refractive index measurement.

Materials

The following enzyme activities were used. A bacterial alpha-amylase with a CBD having the sequence depicted in SEQ ID NO:19 and the same bacterial alpha-amylase but without the CBD module (SEQ ID NO:4). A glucoamylase derived from *Aspergillus niger* having the amino acid sequence shown in WO 00/04136 as SEQ ID NO: 2 or one of the disclosed variants. An acid fungal alpha-amylase derived from *Aspergillus niger*.

Wheat starch (S-5127) was obtained from Sigma-Aldrich.

Example 1

This example illustrates the conversion of granular wheat starch into glucose using a bacterial four module alpha-amylase and a glucoamylase and an acid fungal amylase. A slurry with 33% dry solids (DS) granular starch was prepared by adding 247.5 g of wheat starch under stirring to 502.5 ml of water. The pH was adjusted with HCl to 4.5. The granular starch slurry was distributed to 100 ml blue cap flasks with 75 g in each flask. The flasks were incubated with magnetic stirring in a 60° C. water bath. At zero hours the enzyme activities given in table 1 were dosed to the flasks. Samples were withdrawn after 24, 48, 72, and 96 hours.

TABLE 1

The enzyme activity levels used.

| Bacterial alpha-amylase KNU/kg DS | Glucoamylase AGU/kg DS | Acid fungal alpha-amylase AFAU/kg DS |
|---|---|---|
| 100.0 | 200 | 50 |

Total dry solids starch was determined using the following method. The starch was completely hydrolyzed by adding an excess amount of alpha-amylase (300 KNU/Kg dry solids) and placing the sample in an oil bath at 95° C. for 45 minutes. Subsequently the samples were cooled to 60° C. and an excess amount of glucoamylase (600 AGU/kg DS) was added followed by incubation for 2 hours at 60° C.

Soluble dry solids in the starch hydrolysate were determined by refractive index measurement on samples after filtering through a 0.22 microM filter. The sugar profile was determined by HPLC. The amount of glucose was calculated as DX. The results are shown in tables 2 and 3.

TABLE 2

Soluble dry solids as percentage of total dry substance at 100 KNU/kg DS alpha-amylase dosage.

| KNU/kg DS | 24 hours | 48 hours | 72 hours | 96 hours |
|---|---|---|---|---|
| 100.0 | 92.5 | 96 | 97.3 | 99.2 |

TABLE 3

The DX of the soluble hydrolysate at 100 KNU/kg DS alpha-amylase dosage.

| KNU/kg DS | 24 hours | 48 hours | 72 hours | 96 hours |
|---|---|---|---|---|
| 100.0 | 88.4 | 92.4 | 93.7 | 95.3 |

Example 2

This example illustrates the only partial conversion of granular starch into glucose using a glucoamylase and an acid fungal alpha-amylase.

Flasks with 33% DS granular starch were prepared and incubated as described in example 1. At zero hours the enzyme activities given in table 4 were dosed to the flasks. Samples were withdrawn after 24, 48, 72, and 96 hours. The samples were analyzed as described in examples 1. The results are shown in tables 5 and 6.

TABLE 4

The enzyme activity level used.

| Glucoamylase AGU/kg DS | Acid fungal alpha-amylase AFAU/kg DS |
|---|---|
| 200 | 50 |

TABLE 5

Soluble dry solids as percentage of total dry substance.

| 24 hours | 48 hours | 72 hours | 96 hours |
|---|---|---|---|
| 28.5 | 36.3 | 41.6 | 45.7 |

TABLE 6

DX of the soluble hydrolysate.

| 24 hours | 48 hours | 72 hours | 96 hours |
|---|---|---|---|
| 27.7 | 34.9 | 39.2 | 42.2 |

Example 3

In example 3 conversion of granular wheat starch into glucose was performed using a glucoamylase (200 AGU/kg DS), an acid fungal amylase (50 AFAU/kg DS) and either the intact bacterial four module alpha-amylase (SEQ ID NO:19) also used in example 1 or the same bacterial four module alpha-amylase but without the CBD module (SEQ ID NO:4) (100 KNU/kg DS). A slurry with 33% dry solids (DS) granular starch was prepared and incubated as described in example 1. Samples were withdrawn after 24, 46, 70, and 90 hours.

Total dry solids starch was determined as described in example 1. Soluble dry solids in the starch hydrolysate and the sugar profile were determined as described in example 1. The results are shown in tables 7 and 8.

TABLE 7

Soluble dry solids as percentage of total dry substance. Enzymes: glucoamylase, fungal acid amylase and bacterial alpha-amylase with the CBD module (SEQ ID NO: 19) or without the CBD module (SEQ ID NO: 4).

| | 24 hours | 46 hours | 70 hours | 90 hours |
|---|---|---|---|---|
| Without CBD | 89.7 | 92.4 | 92.4 | 92.5 |
| With CBD | 94.1 | 95.2 | 96.9 | 97.1 |

TABLE 8

The DX of the soluble hydrolysate: Enzymes: glucoamylase, fungal acid amylase and bacterial alpha-amylase with the CBD module (SEQ ID NO: 19) or without the CBD module (SEQ ID NO: 4).

| | 24 hours | 46 hours | 70 hours | 90 hours |
|---|---|---|---|---|
| Without CBD | 85.9 | 88.7 | 89.0 | 89.0 |
| With CBD | 89.9 | 93.3 | 93.0 | 93.2 |

The invention claimed is:

1. A process for producing a soluble starch hydrolyzate, comprising subjecting an aqueous granular starch slurry at a temperature below the initial gelatinization temperature of said granular starch to the action of a first enzyme and a second enzyme, wherein
   (a) the first enzyme
      (i) is a member of Glycoside Hydrolase Family 13;
      (ii) has alpha-1,4-glucosidic hydrolysis activity; and
      (iii) comprises a functional carbohydrate-binding module (CBM) belonging to CBM Family 20, which has an amino acid sequence having at least 90% homology to the amino acid sequence of SEQ ID NO: 3; and
   (b) the second enzyme is a fungal alpha-amylase (EC 3.2.1.1), a beta-amylase (E.C. 3.2.1.2), or a glucoamylase (E.C.3.2.1.3).

2. The process of claim 1, wherein the CBM has an amino acid sequence having at least 95% homology to the amino acid sequence of SEQ ID NO: 3.

3. The process of claim 1, wherein the CBM has an amino acid sequence having at least 98% homology to the amino acid sequence of SEQ ID NO: 3.

4. The process of claim 1, wherein the CBM has an amino acid sequence having at least 99% homology to the amino acid sequence of SEQ ID NO: 3.

5. The process of claim 1, wherein the CBM comprises the amino acid sequence of SEQ ID NO: 3.

6. The process of claim 1, wherein the first enzyme is an alpha-amylase.

7. The process of claim 1, wherein the first enzyme comprises an amino acid sequence having at least 95% homology to the amino acid sequence of SEQ ID NO: 19.

8. The process of claim 1, wherein the first enzyme is a hybrid alpha-amylase.

9. The process of claim 1, wherein the first enzyme is an alpha-amylase which comprises a catalytic domain which has an amino acid sequence having at least 90% homology to the amino acid sequence of SEQ ID NO: 4.

10. The process of claim 1, wherein the first enzyme is an alpha-amylase which comprises a catalytic domain which has an amino acid sequence having at least 95% homology to the amino acid sequence of SEQ ID NO: 4.

11. The process of claim 1, wherein the second enzyme is a fungal alpha-amylase.

12. The process of claim 1, wherein the second enzyme is a beta-amylase.

13. The process of claim 1, wherein the second enzyme is a glucoamylase.

14. The process of claim 1, wherein the starch slurry has 20-55% dry solids granular starch.

15. The process of claim 1, wherein at least 85% of the dry solids of the granular starch is converted into the soluble starch hydrolyzate.

16. The process of claim 1, further comprising subjecting the granular starch slurry to the action of an isoamylase and/or a pullulanase.

17. The process of claim 1, which is conducted at a temperature of at least 58° C.

18. The process of claim 1, which is conducted at a pH of 3-7.

19. The process of claim 1, wherein the soluble starch hydrolyzate has a DX of at least 94.5%.

20. The process of claim 1, wherein the granular starch is obtained from tubers, roots, stems, or whole grain.

21. The process of claim 1, wherein the granular starch is obtained from cereals.

22. The process of claim 1, wherein the granular starch is obtained from corn, cobs, wheat, barley, rye, milo, sago, cassava, tapioca, sorghum, rice or potatoes.

23. The process of claim 1, wherein the granular starch is obtained from dry milling of whole grain or from wet milling of whole grain or from milled corn grits.

24. The process of claim 1, which is conducted in an ultrafiltration system wherein the retentate is held under recirculation in the presence of enzymes, raw starch and water and the permeate is the soluble starch hydrolyzate.

25. The process of claim 1, which is conducted in a continuous membrane reactor with ultrafiltration membranes and wherein the retentate is held under recirculation in the presence of enzymes, raw starch and water and the permeate is the soluble starch hydrolyzate.

26. The process of claim 1, which is conducted in a continuous membrane reactor with microfiltration membranes and wherein the retentate is held under recirculation in presence of enzymes, raw starch and water and the permeate is the soluble starch hydrolyzate.

27. A process for production of high fructose starch-based syrup (HFSS), comprising converting a soluble starch hydrolyzate produced by the process of claim 1 into high fructose starch-based syrup (HFSS).

28. A process for production of a fermentation product, comprising fermenting a soluble starch hydrolyzate produced by the process of claim 1 with a fermenting organism to produce the fermentation product.

29. The process of claim 28, wherein the fermentation product is citric acid, monosodium glutamate, gluconic acid, sodium gluconate, calcium gluconate, potassium gluconate, glucono delta lactone, sodium erythorbate, itaconic acid, lactic acid, gluconic acid; ketones; amino acids, glutamic acid (sodium monoglutaminate), penicillin, tetracyclin; enzymes; vitamins or hormones.

30. A process for production of fuel or potable ethanol, comprising fermenting a soluble starch hydrolyzate produced by the process of claim 1 with a fermenting organism to produce the ethanol.

31. The process of claim 30, wherein the fermentation step is carried out simultaneously or separately/sequential to the hydrolysis of the granular starch.

* * * * *

UNITED STATES PATENT AND TRADEMARK OFFICE
CERTIFICATE OF CORRECTION

PATENT NO.        : 7,998,709 B2                              Page 1 of 1
APPLICATION NO.   : 12/540472
DATED             : August 16, 2011
INVENTOR(S)       : Viksø-Nielsen et al.

It is certified that error appears in the above-identified patent and that said Letters Patent is hereby corrected as shown below:

In the Specification at column 1, line 8, after "Jun. 25, 2004" insert --(now U.S. Patent No. 7,618,795)--.

Signed and Sealed this
Third Day of April, 2012

David J. Kappos
*Director of the United States Patent and Trademark Office*

SEQUENCE LISTING

<160> NUMBER OF SEQ ID NOS: 22

<210> SEQ ID NO 1
<211> LENGTH: 102
<212> TYPE: PRT
<213> ORGANISM: Bacillus flavothermus

<400> SEQUENCE: 1

Ile Ser Thr Thr Ser Gln Ile Thr Phe Thr Val Asn Asn Ala Thr Thr
1               5                   10                  15

Val Trp Gly Gln Asn Val Tyr Val Val Gly Asn Ile Ser Gln Leu Gly
            20                  25                  30

Asn Trp Asp Pro Val His Ala Val Gln Met Thr Pro Ser Ser Tyr Pro
        35                  40                  45

Thr Trp Thr Val Thr Ile Pro Leu Leu Gln Gly Gln Asn Ile Gln Phe
    50                  55                  60

Lys Phe Ile Lys Lys Asp Ser Ala Gly Asn Val Ile Trp Glu Asp Ile
65                  70                  75                  80

Ser Asn Arg Thr Tyr Thr Val Pro Thr Ala Ala Ser Gly Ala Tyr Thr
                85                  90                  95

Ala Ser Trp Asn Val Pro
            100

<210> SEQ ID NO 2
<211> LENGTH: 99
<212> TYPE: PRT
<213> ORGANISM: Bacillus species

<400> SEQUENCE: 2

Thr Ser Asn Val Thr Phe Thr Val Asn Asn Ala Thr Thr Val Tyr Gly
1               5                   10                  15

Gln Asn Val Tyr Val Val Gly Asn Ile Pro Glu Leu Gly Asn Trp Asn
            20                  25                  30

Ile Ala Asn Ala Ile Gln Met Thr Pro Ser Ser Tyr Pro Thr Trp Lys
        35                  40                  45

Thr Thr Val Ser Leu Pro Gln Gly Lys Ala Ile Glu Phe Lys Phe Ile
    50                  55                  60

Lys Lys Asp Ser Ala Gly Asn Val Ile Trp Glu Asn Ile Ala Asn Arg
65                  70                  75                  80

Thr Tyr Thr Val Pro Phe Ser Ser Thr Gly Ser Tyr Thr Ala Asn Trp
                85                  90                  95

Asn Val Pro

<210> SEQ ID NO 3
<211> LENGTH: 102
<212> TYPE: PRT
<213> ORGANISM: Alcaliphilic Bacillus

<400> SEQUENCE: 3

Thr Ser Thr Thr Ser Gln Ile Thr Phe Thr Val Asn Asn Ala Thr Thr
1               5                   10                  15

Val Trp Gly Gln Asn Val Tyr Val Val Gly Asn Ile Ser Gln Leu Gly
            20                  25                  30

Asn Trp Asp Pro Val Asn Ala Val Gln Met Thr Pro Ser Ser Tyr Pro
        35                  40                  45

Thr Trp Val Val Thr Val Pro Leu Pro Gln Ser Gln Asn Ile Gln Phe
    50                  55                  60

```
Lys Phe Ile Lys Lys Asp Gly Ser Gly Asn Val Ile Trp Glu Asn Ile
 65                  70                  75                  80

Ser Asn Arg Thr Tyr Thr Val Pro Thr Ala Ala Ser Gly Ala Tyr Thr
                 85                  90                  95

Ala Asn Trp Asn Val Pro
            100

<210> SEQ ID NO 4
<211> LENGTH: 484
<212> TYPE: PRT
<213> ORGANISM: Bacillus flavothermus

<400> SEQUENCE: 4

Gly Ser Val Pro Val Asn Gly Thr Met Met Gln Tyr Phe Glu Trp Tyr
  1               5                  10                  15

Leu Pro Asp Asp Gly Thr Leu Trp Thr Lys Val Ala Asn Asn Ala Gln
             20                  25                  30

Ser Leu Ala Asn Leu Gly Ile Thr Ala Leu Trp Leu Pro Pro Ala Tyr
         35                  40                  45

Lys Gly Thr Ser Ser Ser Asp Val Gly Tyr Gly Val Tyr Asp Leu Tyr
 50                  55                  60

Asp Leu Gly Glu Phe Asn Gln Lys Gly Thr Val Arg Thr Lys Tyr Gly
 65                  70                  75                  80

Thr Lys Thr Gln Tyr Ile Gln Ala Ile Gln Ala Ala His Thr Ala Gly
                 85                  90                  95

Met Gln Val Tyr Ala Asp Val Val Phe Asn His Lys Ala Gly Ala Asp
            100                 105                 110

Gly Thr Glu Leu Val Asp Ala Val Glu Val Asn Pro Ser Asp Arg Asn
        115                 120                 125

Gln Glu Ile Ser Gly Thr Tyr Gln Ile Gln Ala Trp Thr Lys Phe Asp
130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Thr Gly Lys Ala Trp Asp Trp Glu Val Asp Thr
            180                 185                 190

Glu Asn Gly Asn Tyr Asp Tyr Leu Met Tyr Ala Asp Leu Asp Met Asp
        195                 200                 205

His Pro Glu Val Val Ser Glu Leu Lys Asn Trp Gly Lys Trp Tyr Val
210                 215                 220

Thr Thr Thr Asn Ile Asp Gly Phe Arg Leu Asp Ala Val Lys His Ile
225                 230                 235                 240

Lys Tyr Ser Phe Phe Pro Asp Trp Leu Ser Tyr Val Arg Thr Gln Thr
                245                 250                 255

Gln Lys Pro Leu Phe Ala Val Gly Glu Phe Trp Ser Tyr Asp Ile Ser
            260                 265                 270

Lys Leu His Asn Tyr Ile Thr Lys Thr Asn Gly Ser Met Ser Leu Phe
        275                 280                 285

Asp Ala Pro Leu His Asn Asn Phe Tyr Ile Ala Ser Lys Ser Gly Gly
290                 295                 300

Tyr Phe Asp Met Arg Thr Leu Leu Asn Asn Thr Leu Met Lys Asp Gln
305                 310                 315                 320

Pro Thr Leu Ala Val Thr Leu Val Asp Asn His Asp Thr Glu Pro Gly
                325                 330                 335
```

```
Gln Ser Leu Gln Ser Trp Val Glu Pro Trp Phe Lys Pro Leu Ala Tyr
            340                 345                 350

Ala Phe Ile Leu Thr Arg Gln Glu Gly Tyr Pro Cys Val Phe Tyr Gly
            355                 360                 365

Asp Tyr Tyr Gly Ile Pro Lys Tyr Asn Ile Pro Ala Leu Lys Ser Lys
        370                 375                 380

Leu Asp Pro Leu Leu Ile Ala Arg Arg Asp Tyr Ala Tyr Gly Thr Gln
385                 390                 395                 400

His Asp Tyr Ile Asp Ser Ala Asp Ile Ile Gly Trp Thr Arg Glu Gly
            405                 410                 415

Val Ala Glu Lys Ala Asn Ser Gly Leu Ala Ala Leu Ile Thr Asp Gly
            420                 425                 430

Pro Gly Gly Ser Lys Trp Met Tyr Val Gly Lys Gln His Ala Gly Lys
            435                 440                 445

Thr Phe Tyr Asp Leu Thr Gly Asn Arg Ser Asp Thr Val Thr Ile Asn
            450                 455                 460

Ala Asp Gly Trp Gly Glu Phe Lys Val Asn Gly Ser Val Ser Ile
465                 470                 475                 480

Trp Val Pro Lys

<210> SEQ ID NO 5
<211> LENGTH: 485
<212> TYPE: PRT
<213> ORGANISM: Bacillus species

<400> SEQUENCE: 5

Ala Asn Thr Ala Pro Val Asn Gly Thr Met Met Gln Tyr Phe Glu Trp
1               5                   10                  15

Asp Leu Pro Asn Asp Gly Thr Leu Trp Thr Lys Val Lys Asn Glu Ala
            20                  25                  30

Ser Ser Leu Ser Ala Leu Gly Ile Thr Ala Leu Trp Leu Pro Pro Ala
        35                  40                  45

Tyr Lys Gly Thr Ser Gln Ala Asp Val Gly Tyr Gly Val Tyr Asp Leu
    50                  55                  60

Tyr Asp Leu Gly Glu Phe Asn Gln Lys Gly Thr Ile Arg Thr Lys Tyr
65                  70                  75                  80

Gly Thr Lys Thr Gln Tyr Leu Gln Ala Ile Gln Ala Ala Lys Ser Ala
            85                  90                  95

Gly Met Gln Val Tyr Ala Asp Val Val Phe Asn His Lys Ala Gly Ala
            100                 105                 110

Asp Ser Thr Glu Trp Val Asp Ala Val Glu Val Asn Pro Ser Asn Arg
        115                 120                 125

Asn Gln Glu Thr Ser Gly Thr Tyr Gln Ile Gln Ala Trp Thr Lys Phe
    130                 135                 140

Asp Phe Pro Gly Arg Gly Asn Thr Tyr Ser Ser Phe Lys Trp Arg Trp
145                 150                 155                 160

Tyr His Phe Asp Gly Thr Asp Trp Asp Glu Ser Arg Lys Leu Asn Arg
            165                 170                 175

Ile Tyr Lys Phe Arg Gly Thr Gly Lys Ala Trp Asp Trp Glu Val Asp
            180                 185                 190

Thr Glu Asn Gly Asn Tyr Asp Tyr Leu Met Phe Ala Asp Leu Asp Met
        195                 200                 205

Asp His Pro Glu Val Val Ala Glu Leu Lys Asn Trp Gly Lys Trp Tyr
    210                 215                 220
```

-continued

Val Asn Thr Thr Asn Val Asp Gly Phe Arg Leu Asp Ala Val Lys His
225                 230                 235                 240

Ile Lys Tyr Ser Phe Phe Pro Asp Trp Leu Ser Tyr Val Arg Asn Gln
            245                 250                 255

Thr Gly Lys Asn Leu Phe Ala Val Gly Glu Phe Trp Gly Tyr Asp Val
        260                 265                 270

Asn Lys Leu His Asn Tyr Ile Thr Lys Thr Asn Gly Ala Met Ser Leu
    275                 280                 285

Phe Asp Ala Pro Leu His Asn Asn Phe Tyr Ile Ala Ser Lys Ser Ser
290                 295                 300

Gly Tyr Phe Asp Met Arg Tyr Leu Leu Asn Asn Thr Leu Met Lys Asp
305                 310                 315                 320

Gln Pro Ala Leu Ala Val Thr Leu Val Asp Asn His Asp Thr Gln Pro
                325                 330                 335

Gly Gln Ser Leu Gln Ser Trp Val Glu Pro Trp Phe Lys Pro Leu Ala
            340                 345                 350

Tyr Ala Phe Ile Leu Thr Arg Gln Glu Gly Tyr Pro Cys Val Phe Tyr
        355                 360                 365

Gly Asp Tyr Tyr Gly Ile Pro Lys Tyr Asn Ile Pro Gly Leu Lys Ser
    370                 375                 380

Lys Ile Asp Pro Leu Leu Ile Ala Arg Arg Asp Tyr Ala Tyr Gly Thr
385                 390                 395                 400

Gln Arg Asp Tyr Ile Asp His Gln Asp Ile Ile Gly Trp Thr Arg Glu
                405                 410                 415

Gly Ile Asp Ala Lys Pro Asn Ser Gly Leu Ala Ala Leu Ile Thr Asp
            420                 425                 430

Gly Pro Gly Gly Ser Lys Trp Met Tyr Val Gly Lys Arg His Ala Gly
        435                 440                 445

Lys Val Phe Tyr Asp Leu Thr Gly Asn Arg Ser Asp Thr Val Thr Ile
    450                 455                 460

Asn Ala Asp Gly Trp Gly Glu Phe Lys Val Asn Gly Gly Ser Val Ser
465                 470                 475                 480

Ile Trp Val Ala Lys
            485

<210> SEQ ID NO 6
<211> LENGTH: 484
<212> TYPE: PRT
<213> ORGANISM: Alkaliphilic bacillus

<400> SEQUENCE: 6

Gly Ser Val Pro Val Asn Gly Thr Met Met Gln Tyr Phe Glu Trp Tyr
1               5                   10                  15

Leu Pro Asp Asp Gly Thr Leu Trp Thr Lys Val Ala Asn Asn Ala Gln
            20                  25                  30

Ser Leu Ala Asn Leu Gly Ile Thr Ala Leu Trp Leu Pro Pro Ala Tyr
        35                  40                  45

Lys Gly Thr Ser Ser Ser Asp Val Gly Tyr Gly Val Tyr Asp Leu Tyr
    50                  55                  60

Asp Leu Gly Glu Phe Asn Gln Lys Gly Thr Val Arg Thr Lys Tyr Gly
65                  70                  75                  80

Thr Lys Thr Gln Tyr Ile Gln Ala Ile Gln Ala Ala His Thr Ala Gly
                85                  90                  95

Met Gln Val Tyr Ala Asp Val Val Phe Asn His Lys Ala Gly Ala Asp
            100                 105                 110

Gly Thr Glu Leu Val Asp Ala Val Glu Val Asn Pro Ser Asp Arg Asn
            115                 120                 125

Gln Glu Ile Ser Gly Thr Tyr Gln Ile Gln Ala Trp Thr Lys Phe Asp
130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Thr Gly Lys Ala Trp Asp Trp Glu Val Asp Thr
            180                 185                 190

Glu Asn Gly Asn Tyr Asp Tyr Leu Met Tyr Ala Asp Leu Asp Met Asp
        195                 200                 205

His Pro Glu Val Val Ser Glu Leu Lys Asn Trp Gly Lys Trp Tyr Val
210                 215                 220

Ile Thr Thr Asn Ile Asp Gly Phe Arg Leu Asp Ala Val Lys His Ile
225                 230                 235                 240

Lys Tyr Ser Phe Phe Pro Asp Trp Leu Ser Tyr Leu Arg Thr Gln Thr
                245                 250                 255

Gln Lys Pro Leu Phe Ala Val Gly Glu Phe Trp Ser Tyr Asp Ile Asn
            260                 265                 270

Lys Leu His Asn Tyr Ile Thr Lys Thr Asn Gly Ser Met Ser Leu Phe
        275                 280                 285

Asp Ala Pro Leu His Asn Asn Phe Tyr Ile Ala Ser Lys Ser Gly Gly
290                 295                 300

Tyr Phe Asp Met Arg Thr Leu Leu Asn Asn Thr Leu Met Lys Glu Gln
305                 310                 315                 320

Pro Thr Leu Ser Val Thr Leu Val Asp Asn His Asp Thr Glu Pro Gly
                325                 330                 335

Gln Ser Leu Gln Ser Trp Val Glu Pro Trp Phe Lys Pro Leu Ala Tyr
            340                 345                 350

Ala Phe Ile Leu Thr Arg Gln Glu Gly Tyr Pro Cys Val Phe Tyr Gly
        355                 360                 365

Asp Tyr Tyr Gly Ile Pro Lys Tyr Asn Ile Pro Ala Leu Lys Ser Lys
370                 375                 380

Leu Asp Pro Leu Leu Ile Ala Arg Arg Asp Tyr Ala Tyr Gly Thr Gln
385                 390                 395                 400

His Asp Tyr Ile Asp Asn Ala Asp Ile Ile Gly Trp Thr Arg Glu Gly
                405                 410                 415

Val Ala Glu Lys Ala Asn Ser Gly Leu Ala Ala Leu Ile Thr Asp Gly
            420                 425                 430

Pro Gly Gly Ser Lys Trp Met Tyr Val Gly Lys Gln His Ala Gly Lys
        435                 440                 445

Thr Phe Tyr Asp Leu Thr Gly Asn Arg Ser Asp Thr Val Thr Ile Asn
450                 455                 460

Ala Asp Gly Trp Gly Glu Phe Lys Val Asn Gly Gly Ser Val Ser Ile
465                 470                 475                 480

Trp Val Pro Lys

<210> SEQ ID NO 7
<211> LENGTH: 517
<212> TYPE: PRT
<213> ORGANISM: Bacillus species

<400> SEQUENCE: 7

Met Ser Leu Phe Lys Lys Ile Phe Pro Trp Ile Leu Ser Leu Leu Leu

-continued

```
1               5                   10                  15
Leu Phe Leu Phe Ile Ala Pro Phe Ser Ile Gln Thr Glu Lys Val Arg
                20                  25                  30

Ala Gly Ser Val Pro Val Asn Gly Thr Met Met Gln Tyr Phe Glu Trp
                35                  40                  45

Tyr Leu Pro Asp Asp Gly Thr Leu Trp Thr Lys Val Ala Asn Asn Ala
                50                  55                  60

Gln Ser Leu Ala Asn Leu Gly Ile Thr Ala Leu Trp Leu Pro Pro Ala
65                  70                  75                  80

Tyr Lys Gly Thr Ser Ser Asp Val Gly Tyr Gly Val Tyr Asp Leu
                    85                  90                  95

Tyr Asp Leu Gly Glu Phe Asn Gln Lys Gly Thr Val Arg Thr Lys Tyr
                100                 105                 110

Gly Thr Lys Thr Gln Tyr Ile Gln Ala Ile Gln Ala Ala His Thr Ala
                115                 120                 125

Gly Met Gln Val Tyr Ala Asp Val Val Phe Asn His Lys Ala Gly Ala
                130                 135                 140

Asp Gly Thr Glu Leu Val Asp Ala Val Glu Val Asn Pro Ser Asp Arg
145                 150                 155                 160

Asn Gln Glu Ile Ser Gly Thr Tyr Gln Ile Gln Ala Trp Thr Lys Phe
                165                 170                 175

Asp Phe Pro Gly Arg Gly Asn Thr Tyr Ser Ser Phe Lys Trp Arg Trp
                180                 185                 190

Tyr His Phe Asp Gly Thr Asp Trp Asp Glu Ser Arg Lys Leu Asn Arg
                195                 200                 205

Ile Tyr Lys Phe Arg Gly Thr Gly Lys Ala Trp Asp Trp Glu Val Asp
                210                 215                 220

Thr Glu Asn Gly Asn Tyr Asp Tyr Leu Met Tyr Ala Asp Leu Asp Met
225                 230                 235                 240

Asp His Pro Glu Val Val Ser Glu Leu Lys Asn Trp Gly Lys Trp Tyr
                245                 250                 255

Val Thr Thr Thr Asn Ile Asp Gly Phe Arg Leu Asp Ala Val Lys His
                260                 265                 270

Ile Lys Tyr Ser Phe Phe Pro Asp Trp Leu Ser Tyr Val Arg Thr Gln
                275                 280                 285

Thr Gln Lys Pro Leu Phe Ala Val Gly Glu Phe Trp Ser Tyr Asp Ile
                290                 295                 300

Ser Lys Leu His Asn Tyr Ile Thr Lys Thr Asn Gly Ser Met Ser Leu
305                 310                 315                 320

Phe Asp Ala Pro Leu His Asn Asn Phe Tyr Ile Ala Ser Lys Ser Gly
                325                 330                 335

Gly Tyr Phe Asp Met Arg Thr Leu Leu Asn Asn Thr Leu Met Lys Asp
                340                 345                 350

Gln Pro Thr Leu Ala Val Thr Leu Val Asp Asn His Asp Thr Glu Pro
                355                 360                 365

Gly Gln Ser Leu Gln Ser Trp Val Glu Pro Trp Phe Lys Pro Leu Ala
                370                 375                 380

Tyr Ala Phe Ile Leu Thr Arg Gln Glu Gly Tyr Pro Cys Val Phe Tyr
385                 390                 395                 400

Gly Asp Tyr Tyr Gly Ile Pro Lys Tyr Asn Ile Pro Ala Leu Lys Ser
                405                 410                 415

Lys Leu Asp Pro Leu Leu Ile Ala Arg Arg Asp Tyr Ala Tyr Gly Thr
                420                 425                 430
```

```
Gln His Asp Tyr Ile Asp Ser Ala Asp Ile Ile Gly Trp Thr Arg Glu
        435                 440                 445

Gly Val Ala Glu Lys Ala Asn Ser Gly Leu Ala Ala Leu Ile Thr Asp
    450                 455                 460

Gly Pro Gly Gly Ser Lys Trp Met Tyr Val Gly Lys Gln His Ala Gly
465                 470                 475                 480

Lys Thr Phe Tyr Asp Leu Thr Gly Asn Arg Ser Asp Thr Val Thr Ile
                485                 490                 495

Asn Ala Asp Gly Trp Gly Glu Phe Lys Val Asn Gly Gly Ser Val Ser
            500                 505                 510

Ile Trp Val Pro Lys
        515

<210> SEQ ID NO 8
<211> LENGTH: 550
<212> TYPE: PRT
<213> ORGANISM: Unknown
<220> FEATURE:
<223> OTHER INFORMATION: Synthetic Construct

<400> SEQUENCE: 8

Met Ser Leu Phe Lys Lys Ile Phe Pro Trp Ile Val Ser Leu Leu Leu
1               5                   10                  15

Leu Phe Ser Phe Ile Ala Pro Phe Ser Ile Gln Thr Glu Lys Val Arg
            20                  25                  30

Ala Gly Ser Val Pro Val Asn Gly Thr Met Met Gln Tyr Phe Glu Trp
        35                  40                  45

Tyr Leu Pro Asp Asp Gly Thr Leu Trp Thr Lys Val Ala Asn Asn Ala
    50                  55                  60

Gln Ser Leu Ala Asn Leu Gly Ile Thr Ala Leu Trp Leu Pro Pro Ala
65                  70                  75                  80

Tyr Lys Gly Thr Ser Ser Ser Asp Val Gly Tyr Gly Val Tyr Asp Leu
                85                  90                  95

Tyr Asp Leu Gly Glu Phe Asn Gln Lys Gly Thr Val Arg Thr Lys Tyr
            100                 105                 110

Gly Thr Lys Thr Gln Tyr Ile Gln Ala Ile Gln Ala Ala His Thr Ala
        115                 120                 125

Gly Met Gln Val Tyr Ala Asp Val Val Phe Asn His Lys Ala Gly Ala
    130                 135                 140

Asp Gly Thr Glu Leu Val Asp Ala Val Glu Val Asn Pro Ser Asp Arg
145                 150                 155                 160

Asn Gln Glu Ile Ser Gly Thr Tyr Gln Ile Gln Ala Trp Thr Lys Phe
                165                 170                 175

Asp Phe Pro Gly Arg Gly Asn Thr Tyr Ser Ser Phe Lys Trp Arg Trp
            180                 185                 190

Tyr His Phe Asp Gly Thr Asp Trp Asp Glu Ser Arg Lys Leu Asn Arg
        195                 200                 205

Ile Tyr Lys Phe Arg Gly Thr Gly Lys Ala Trp Asp Trp Glu Val Asp
    210                 215                 220

Thr Glu Asn Gly Asn Tyr Asp Tyr Leu Met Tyr Ala Asp Leu Asp Met
225                 230                 235                 240

Asp His Pro Glu Val Val Ser Glu Leu Lys Asn Trp Gly Lys Trp Tyr
                245                 250                 255

Val Thr Thr Thr Asn Ile Asp Gly Phe Arg Leu Asp Ala Val Lys His
            260                 265                 270

Ile Lys Tyr Ser Phe Phe Pro Asp Trp Leu Ser Tyr Val Arg Thr Gln
```

```
                275                 280                 285
Thr Gln Lys Pro Leu Phe Ala Val Gly Glu Phe Trp Ser Tyr Asp Ile
290                 295                 300

Asn Lys Leu His Asn Tyr Ile Thr Lys Thr Asn Gly Ser Met Ser Leu
305                 310                 315                 320

Phe Asp Ala Pro Leu His Asn Asn Phe Tyr Ile Ala Ser Lys Ser Gly
                325                 330                 335

Gly Tyr Phe Asp Met Arg Thr Leu Leu Asn Asn Thr Leu Met Lys Asp
                340                 345                 350

Gln Pro Thr Leu Ser Val Thr Leu Val Asp Asn His Asp Thr Glu Pro
                355                 360                 365

Gly Gln Ser Leu Gln Ser Trp Val Glu Pro Trp Phe Lys Pro Leu Ala
370                 375                 380

Tyr Ala Phe Ile Leu Thr Arg Gln Glu Gly Tyr Pro Cys Ile Phe Tyr
385                 390                 395                 400

Gly Asp Tyr Tyr Gly Ile Pro Lys Tyr Asn Ile Pro Ala Leu Lys Ser
                405                 410                 415

Lys Leu Asp Pro Leu Leu Ile Ala Arg Arg Asp Tyr Ala Tyr Gly Thr
                420                 425                 430

Gln His Asp Tyr Ile Asp Asn Ala Asp Ile Ile Gly Trp Thr Arg Glu
                435                 440                 445

Gly Val Ala Glu Lys Ala Asn Ser Gly Leu Ala Ala Leu Ile Thr Asp
450                 455                 460

Gly Pro Gly Gly Ser Lys Trp Met Tyr Val Gly Lys Gln His Ala Gly
465                 470                 475                 480

Lys Thr Phe Tyr Asp Leu Thr Gly Asn Arg Ser Asp Thr Val Thr Ile
                485                 490                 495

Asn Ala Asp Gly Trp Gly Glu Phe Lys Val Asn Gly Gly Ser Val Ser
                500                 505                 510

Ile Trp Val Pro Lys Thr Ser Thr Ser Gln Ile Thr Phe Thr Val
                515                 520                 525

Asn Asn Ala Thr Thr Val Trp Gly Gln Asn Val Tyr Val Val Gly Asn
530                 535                 540

Ile Ser Gln Leu Gly Asn
545                 550

<210> SEQ ID NO 9
<211> LENGTH: 482
<212> TYPE: PRT
<213> ORGANISM: Unknown
<220> FEATURE:
<223> OTHER INFORMATION: Synthetic Construct

<400> SEQUENCE: 9

Ala Pro Val Asn Gly Thr Met Met Gln Tyr Phe Glu Trp Asp Leu Pro
1               5                   10                  15

Asn Asp Gly Thr Leu Trp Thr Lys Val Lys Asn Glu Ala Thr Asn Leu
                20                  25                  30

Ser Ser Leu Gly Ile Thr Ala Leu Trp Leu Pro Pro Ala Tyr Lys Gly
            35                  40                  45

Thr Ser Gln Ser Asp Val Gly Tyr Gly Val Tyr Asp Leu Tyr Asp Leu
        50                  55                  60

Gly Glu Phe Asn Gln Lys Gly Thr Ile Arg Thr Lys Tyr Gly Thr Lys
65                  70                  75                  80

Ala Gln Tyr Ile Gln Ala Ile Gln Ala Ala Lys Ala Ala Gly Met Gln
                85                  90                  95
```

Val Tyr Ala Asp Val Val Phe Asn His Lys Ala Gly Ala Asp Gly Thr
100                     105                     110

Glu Phe Val Asp Ala Val Glu Val Asn Pro Ser Asn Arg Asn Gln Glu
        115                     120                     125

Thr Ser Gly Thr Tyr Gln Ile Gln Ala Trp Thr Lys Phe Asp Phe Pro
130                     135                     140

Gly Arg Gly Asn Thr Tyr Ser Ser Phe Lys Trp Arg Trp Tyr His Phe
145                     150                     155                 160

Asp Gly Thr Asp Trp Asp Glu Ser Arg Lys Leu Asn Arg Ile Tyr Lys
                165                     170                     175

Phe Arg Gly Thr Gly Lys Ala Trp Asp Trp Glu Val Asp Thr Glu Asn
                180                     185                     190

Gly Asn Tyr Asp Tyr Leu Met Phe Ala Asp Leu Asp Met Asp His Pro
                195                     200                     205

Glu Val Val Thr Glu Leu Lys Asn Trp Gly Lys Trp Tyr Val Asn Thr
210                     215                     220

Thr Asn Val Asp Gly Phe Arg Leu Asp Ala Val Lys His Ile Lys Tyr
225                     230                     235                 240

Ser Phe Phe Pro Asp Trp Leu Thr Tyr Val Arg Asn Gln Thr Gly Lys
                245                     250                     255

Asn Leu Phe Ala Val Gly Glu Phe Trp Ser Tyr Asp Val Asn Lys Leu
                260                     265                     270

His Asn Tyr Ile Thr Lys Thr Asn Gly Ser Met Ser Leu Phe Asp Ala
                275                     280                     285

Pro Leu His Asn Asn Phe Tyr Ile Ala Ser Lys Ser Ser Gly Tyr Phe
                290                     295                     300

Asp Met Arg Tyr Leu Leu Asn Asn Thr Leu Met Lys Asp Gln Pro Ser
305                     310                     315                 320

Leu Ala Val Thr Leu Val Asp Asn His Asp Thr Gln Pro Gly Gln Ser
                325                     330                     335

Leu Gln Ser Trp Val Glu Ala Trp Phe Lys Pro Leu Ala Tyr Ala Phe
                340                     345                     350

Ile Leu Thr Arg Gln Glu Gly Tyr Pro Cys Val Phe Tyr Gly Asp Tyr
                355                     360                     365

Tyr Gly Ile Pro Lys Tyr Asn Ile Pro Gly Leu Lys Ser Lys Ile Asp
                370                     375                     380

Pro Leu Leu Ile Ala Arg Arg Asp Tyr Ala Tyr Gly Thr Gln Arg Asp
385                     390                     395                 400

Tyr Ile Asp His Gln Asp Ile Ile Gly Trp Thr Arg Glu Gly Ile Asp
                405                     410                     415

Ala Lys Pro Asn Ser Gly Leu Ala Ala Leu Ile Thr Asp Gly Pro Gly
                420                     425                     430

Gly Ser Lys Trp Met Tyr Val Gly Lys Lys His Ala Gly Lys Val Phe
                435                     440                     445

Tyr Asp Leu Thr Gly Asn Arg Ser Asp Thr Val Thr Ile Asn Ala Asp
                450                     455                     460

Gly Trp Gly Glu Phe Lys Val Asn Gly Gly Ser Val Ser Ile Trp Val
465                     470                     475                 480

Ala Lys

<210> SEQ ID NO 10
<211> LENGTH: 482
<212> TYPE: PRT
<213> ORGANISM: Unknown

<220> FEATURE:
<223> OTHER INFORMATION: Synthetic construct

<400> SEQUENCE: 10

```
Ala Pro Val Asn Gly Thr Met Met Gln Tyr Phe Glu Trp Asp Leu Pro
1               5                   10                  15

Asn Asp Gly Thr Leu Trp Thr Lys Val Lys Asn Glu Ala Thr Asn Leu
            20                  25                  30

Ser Ser Leu Gly Ile Thr Ala Leu Trp Leu Pro Pro Ala Tyr Lys Gly
        35                  40                  45

Thr Ser Gln Ser Asp Val Gly Tyr Gly Val Tyr Asp Leu Tyr Asp Leu
    50                  55                  60

Gly Glu Phe Asn Gln Lys Gly Thr Ile Arg Thr Lys Tyr Gly Thr Lys
65              70                  75                  80

Thr Gln Tyr Ile Gln Ala Ile Gln Thr Ala Gln Ala Gly Met Gln
                85                  90                  95

Val Tyr Ala Asp Val Val Phe Asn His Lys Ala Gly Ala Asp Ser Thr
                100                 105                 110

Glu Phe Val Asp Ala Val Glu Val Asn Pro Ser Asn Arg Asn Gln Glu
            115                 120                 125

Thr Ser Gly Thr Tyr Gln Ile Gln Ala Trp Thr Lys Phe Asp Phe Pro
    130                 135                 140

Gly Arg Gly Asn Thr Tyr Ser Ser Phe Lys Trp Arg Trp Tyr His Phe
145                 150                 155                 160

Asp Gly Thr Asp Trp Asp Glu Ser Arg Lys Leu Asn Arg Ile Tyr Lys
                165                 170                 175

Phe Arg Gly Thr Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
        195                 200                 205

Glu Val Val Thr Glu Leu Lys Asn Trp Gly Thr Trp Tyr Val Asn Thr
    210                 215                 220

Thr Asn Ile Asp Gly Phe Arg Leu Asp Ala Val Lys His Ile Lys Tyr
225                 230                 235                 240

Ser Phe Phe Pro Asp Trp Leu Thr Tyr Val Arg Asn Gln Thr Gly Lys
                245                 250                 255

Asn Leu Phe Ala Val Gly Glu Phe Trp Ser Tyr Asp Val Asn Lys Leu
            260                 265                 270

His Asn Tyr Ile Thr Lys Thr Asn Gly Ser Met Ser Leu Phe Asp Ala
        275                 280                 285

Pro Leu His Asn Asn Phe Tyr Thr Ala Ser Lys Ser Ser Gly Tyr Phe
    290                 295                 300

Asp Met Arg Tyr Leu Leu Asn Asn Thr Leu Met Lys Asp Gln Pro Ser
305                 310                 315                 320

Leu Ala Val Thr Leu Val Asp Asn His Asp Thr Gln Pro Gly Gln Ser
                325                 330                 335

Leu Gln Ser Trp Val Glu Pro Trp Phe Lys Gln Leu Ala Tyr Ala Phe
            340                 345                 350

Ile Leu Thr Arg Gln Glu Gly Tyr Pro Cys Val Phe Tyr Gly Asp Tyr
        355                 360                 365

Tyr Gly Ile Pro Lys Tyr Asn Ile Pro Gly Leu Lys Ser Lys Ile Asp
    370                 375                 380

Pro Leu Leu Ile Ala Arg Arg Asp Tyr Ala Tyr Gly Thr Gln Arg Asp
385                 390                 395                 400
```

Tyr Ile Asp His Gln Asp Ile Ile Gly Trp Thr Arg Glu Gly Ile Asp
                405                 410                 415

Ala Lys Pro Asn Ser Gly Leu Ala Ala Leu Ile Thr Asp Gly Pro Gly
            420                 425                 430

Gly Ser Lys Trp Met Tyr Val Gly Lys Lys His Ala Gly Lys Val Phe
        435                 440                 445

Tyr Asp Leu Thr Gly Asn Arg Ser Asp Thr Val Thr Ile Asn Ala Asp
    450                 455                 460

Gly Trp Gly Glu Phe Lys Val Asn Gly Gly Ser Val Ser Ile Trp Val
465                 470                 475                 480

Ala Lys

<210> SEQ ID NO 11
<211> LENGTH: 482
<212> TYPE: PRT
<213> ORGANISM: Unknown
<220> FEATURE:
<223> OTHER INFORMATION: Synthetic construct

<400> SEQUENCE: 11

Ala Pro Val Asn Gly Thr Met Met Gln Tyr Phe Glu Trp Asp Leu Pro
1               5                   10                  15

Asn Asp Gly Thr Leu Trp Thr Lys Val Lys Asn Glu Ala Ser Ser Leu
            20                  25                  30

Ser Ser Leu Gly Ile Thr Ala Leu Trp Leu Pro Pro Ala Tyr Lys Gly
        35                  40                  45

Thr Ser Gln Gly Asp Val Gly Tyr Gly Val Tyr Asp Leu Tyr Asp Leu
    50                  55                  60

Gly Glu Phe Asn Gln Lys Gly Thr Ile Arg Thr Lys Tyr Gly Thr Lys
65                  70                  75                  80

Thr Gln Tyr Leu Gln Ala Ile Gln Ala Ala Lys Ser Ala Gly Met Gln
                85                  90                  95

Val Tyr Ala Asp Val Val Phe Asn His Lys Ala Gly Ala Asp Ser Thr
            100                 105                 110

Glu Trp Val Asp Ala Val Glu Val Asn Pro Ser Asn Arg Asn Gln Glu
        115                 120                 125

Thr Ser Gly Thr Tyr Gln Ile Gln Ala Trp Thr Lys Phe Asp Phe Pro
    130                 135                 140

Gly Arg Gly Asn Thr Tyr Ser Ser Phe Lys Trp Arg Trp Tyr His Phe
145                 150                 155                 160

Asp Gly Thr Asp Trp Asp Glu Ser Arg Lys Leu Asn Arg Ile Tyr Lys
                165                 170                 175

Phe Arg Gly Thr Gly Lys Ala Trp Asp Trp Glu Val Asp Thr Glu Asn
            180                 185                 190

Gly Asn Tyr Asp Tyr Leu Met Phe Ala Asp Leu Asp Met Asp His Pro
        195                 200                 205

Glu Val Val Thr Glu Leu Lys Asn Trp Gly Thr Trp Tyr Val Asn Thr
    210                 215                 220

Thr Asn Val Asp Gly Phe Arg Leu Asp Ala Val Lys His Ile Lys Tyr
225                 230                 235                 240

Ser Phe Phe Pro Asp Trp Leu Thr His Val Arg Ser Gln Thr Arg Lys
                245                 250                 255

Asn Leu Phe Ala Val Gly Glu Phe Trp Ser Tyr Asp Val Asn Lys Leu
            260                 265                 270

His Asn Tyr Ile Thr Lys Thr Ser Gly Thr Met Ser Leu Phe Asp Ala
        275                 280                 285

```
Pro Leu His Asn Asn Phe Tyr Thr Ala Ser Lys Ser Ser Gly Tyr Phe
    290                 295                 300

Asp Met Arg Tyr Leu Leu Asn Asn Thr Leu Met Lys Asp Gln Pro Ser
305                 310                 315                 320

Leu Ala Val Thr Leu Val Asp Asn His Asp Thr Gln Pro Gly Gln Ser
                325                 330                 335

Leu Gln Ser Trp Val Glu Pro Trp Phe Lys Pro Leu Ala Tyr Ala Phe
            340                 345                 350

Ile Leu Thr Arg Gln Glu Gly Tyr Pro Cys Val Phe Tyr Gly Asp Tyr
        355                 360                 365

Tyr Gly Ile Pro Lys Tyr Asn Ile Pro Gly Leu Lys Ser Lys Ile Asp
    370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                405                 410                 415

Ser Lys Pro Asn Ser Gly Leu Ala Ala Leu Ile Thr Asp Gly Pro Gly
            420                 425                 430

Gly Ser Lys Trp Met Tyr Val Gly Lys Lys His Ala Gly Lys Val Phe
        435                 440                 445

Tyr Asp Leu Thr Gly Asn Arg Ser Asp Thr Val Thr Ile Asn Ala Asp
    450                 455                 460

Gly Trp Gly Glu Phe Lys Val Asn Gly Gly Ser Val Ser Ile Trp Val
465                 470                 475                 480

Ala Lys

<210> SEQ ID NO 12
<211> LENGTH: 482
<212> TYPE: PRT
<213> ORGANISM: Unknown
<220> FEATURE:
<223> OTHER INFORMATION: Synthetic construct

<400> SEQUENCE: 12

Ala Pro Val Asn Gly Thr Met Met Gln Tyr Phe Glu Trp Asp Leu Pro
1               5                   10                  15

Asn Asp Gly Thr Leu Trp Thr Lys Val Lys Asn Glu Ala Ser Ser Leu
                20                  25                  30

Ser Ser Leu Gly Ile Thr Ala Leu Trp Leu Pro Pro Ala Tyr Lys Gly
            35                  40                  45

Thr Ser Gln Gly Asp Val Gly Tyr Gly Val Tyr Asp Leu Tyr Asp Leu
        50                  55                  60

Gly Glu Phe Asn Gln Lys Gly Thr Ile Arg Thr Lys Tyr Gly Thr Lys
65                  70                  75                  80

Thr Gln Tyr Leu Gln Ala Ile Gln Ala Ala Lys Ser Ala Gly Met Gln
                85                  90                  95

Val Tyr Ala Asp Val Val Phe Asn His Lys Ala Gly Ala Asp Ser Thr
            100                 105                 110

Glu Trp Val Asp Ala Val Glu Val Asn Pro Ser Asn Arg Asn Gln Glu
        115                 120                 125

Thr Ser Gly Thr Tyr Gln Ile Gln Ala Trp Thr Lys Phe Asp Phe Pro
    130                 135                 140

Asp Arg Gly Asn Thr Tyr Ser Ser Phe Lys Trp Arg Trp Tyr His Phe
145                 150                 155                 160

Asp Gly Thr Asp Trp Asp Glu Ser Arg Lys Leu Asn Arg Ile Tyr Lys
```

```
                    165                 170                 175
Phe Arg Gly Thr Gly Lys Ala Trp Asp Trp Glu Val Asp Thr Glu Asn
                180                 185                 190

Gly Asn Tyr Asp Tyr Leu Met Phe Ala Asp Leu Asp Met Asp His Pro
            195                 200                 205

Glu Val Val Thr Glu Leu Lys Asn Trp Gly Thr Trp Tyr Val Asn Thr
        210                 215                 220

Thr Asn Val Asp Gly Phe Arg Leu Asp Ala Val Lys His Ile Lys Tyr
225                 230                 235                 240

Ser Phe Phe Pro Asp Trp Leu Thr Tyr Val Arg Ser Gln Thr Gln Lys
                245                 250                 255

Asn Leu Phe Ala Val Gly Glu Phe Trp Ser Tyr Asp Val Asn Lys Leu
            260                 265                 270

His Asn Tyr Ile Thr Lys Thr Gly Thr Met Ser Leu Phe Asp Ala
        275                 280                 285

Pro Leu His Asn Asn Phe Tyr Thr Ala Ser Lys Ser Ser Gly Tyr Phe
        290                 295                 300

Asp Met Arg Tyr Leu Leu Asn Asn Thr Leu Met Lys Asp Gln Pro Ser
305                 310                 315                 320

Leu Ala Val Thr Leu Val Asp Asn His Asp Thr Gln Pro Gly Gln Ser
                325                 330                 335

Leu Gln Ser Trp Val Glu Pro Trp Phe Lys Pro Leu Ala Tyr Ala Phe
            340                 345                 350

Ile Leu Thr Arg Gln Glu Gly Tyr Pro Cys Val Phe Tyr Gly Asp Tyr
        355                 360                 365

Tyr Gly Ile Pro Lys Tyr Asn Ile Pro Gly Leu Lys Ser Lys Ile Asp
    370                 375                 380

Pro Leu Leu Ile Ala Arg Arg Asp Tyr Ala Tyr Gly Thr Gln Arg Asp
385                 390                 395                 400

Tyr Ile Asp His Gln Asp Ile Ile Gly Trp Thr Arg Glu Gly Ile Asp
                405                 410                 415

Ser Lys Pro Asn Ser Gly Leu Ala Ala Leu Ile Thr Asp Gly Pro Gly
            420                 425                 430

Gly Ser Lys Trp Met Tyr Val Gly Lys Lys His Ala Gly Lys Val Phe
        435                 440                 445

Tyr Asp Leu Thr Gly Asn Arg Ser Asp Thr Val Thr Ile Asn Ala Asp
    450                 455                 460

Gly Trp Gly Glu Phe Lys Val Asn Gly Gly Ser Val Ser Ile Trp Val
465                 470                 475                 480

Ala Lys

<210> SEQ ID NO 13
<211> LENGTH: 483
<212> TYPE: PRT
<213> ORGANISM: Bacillus licheniformis

<400> SEQUENCE: 13

Ala Asn Leu Asn Gly Thr Leu Met Gln Tyr Phe Glu Trp Tyr Met Pro
1               5                   10                  15

Asn Asp Gly Gln His Trp Arg Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60
```

```
Gly Glu Phe His Gln Lys Gly Thr Val Arg Thr Lys Tyr Gly Thr Lys
 65                  70                  75                  80

Gly Glu Leu Gln Ser Ala Ile Lys Ser Leu His Ser Arg Asp Ile Asn
                 85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
        195                 200                 205

Ala Ala Glu Ile Lys Arg Trp Gly Thr Trp Tyr Ala Asn Glu Leu Gln
210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
        275                 280                 285

His Tyr Gln Phe His Ala Ala Ser Thr Gln Gly Gly Gly Tyr Asp Met
290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Asp Ser Gln Arg Glu Ile Pro Ala Leu Lys His Lys Ile
370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
            420                 425                 430

Gly Gly Ala Lys Arg Met Tyr Val Gly Arg Gln Asn Ala Gly Glu Thr
        435                 440                 445

Trp His Asp Ile Thr Gly Asn Arg Ser Glu Pro Val Val Ile Asn Ser
450                 455                 460

Glu Gly Trp Gly Glu Phe His Val Asn Gly Gly Ser Val Ser Ile Tyr
465                 470                 475                 480

Val Gln Arg
```

<210> SEQ ID NO 14
<211> LENGTH: 483
<212> TYPE: PRT
<213> ORGANISM: Bacillus amyloliquefacience

<400> SEQUENCE: 14

```
Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
            20                  25                  30

Ile Gly Ile Thr Ala Val Trp Ile Pro Pro Ala Tyr Lys Gly Leu Ser
        35                  40                  45

Gln Ser Asp Asn Gly Tyr Gly Pro Tyr Asp Leu Tyr Asp Leu Gly Glu
    50                  55                  60

Phe Gln Gln Lys Gly Thr Val Arg Thr Lys Tyr Gly Thr Lys Ser Glu
65                  70                  75                  80

Leu Gln Asp Ala Ile Gly Ser Leu His Ser Arg Asn Val Gln Val Tyr
                85                  90                  95

Gly Asp Val Val Leu Asn His Lys Ala Gly Ala Asp Ala Thr Glu Asp
            100                 105                 110

Val Thr Ala Val Glu Val Asn Pro Ala Asn Arg Asn Gln Glu Thr Ser
        115                 120                 125

Glu Glu Tyr Gln Ile Lys Ala Trp Thr Asp Phe Arg Phe Pro Gly Arg
    130                 135                 140

Gly Asn Thr Tyr Ser Asp Phe Lys Trp His Trp Tyr His Phe Asp Gly
145                 150                 155                 160

Ala Asp Trp Asp Glu Ser Arg Lys Ile Ser Arg Ile Phe Lys Phe Arg
                165                 170                 175

Gly Glu Gly Lys Ala Trp Asp Trp Glu Val Ser Ser Glu Asn Gly Asn
            180                 185                 190

Tyr Asp Tyr Leu Met Tyr Ala Asp Val Asp Tyr Asp His Pro Asp Val
        195                 200                 205

Val Ala Glu Thr Lys Lys Trp Gly Ile Trp Tyr Ala Asn Glu Leu Ser
    210                 215                 220

Leu Asp Gly Phe Arg Ile Asp Ala Ala Lys His Ile Lys Phe Ser Phe
225                 230                 235                 240

Leu Arg Asp Trp Val Gln Ala Val Arg Gln Ala Thr Gly Lys Glu Met
                245                 250                 255

Phe Thr Val Ala Glu Tyr Trp Gln Asn Asn Ala Gly Lys Leu Glu Asn
            260                 265                 270

Tyr Leu Asn Lys Thr Ser Phe Asn Gln Ser Val Phe Asp Val Pro Leu
        275                 280                 285

His Phe Asn Leu Gln Ala Ala Ser Ser Gln Gly Gly Gly Tyr Asp Met
    290                 295                 300

Arg Arg Leu Leu Asp Gly Thr Val Val Ser Arg His Pro Glu Lys Ala
305                 310                 315                 320

Val Thr Phe Val Glu Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Thr Ser Pro Lys Glu Ile Pro Ser Leu Lys Asp Asn Ile
    370                 375                 380
```

-continued

Glu Pro Ile Leu Lys Ala Arg Lys Glu Tyr Ala Tyr Gly Pro Gln His
385                 390                 395                 400

Asp Tyr Ile Asp His Pro Asp Val Ile Gly Trp Thr Arg Glu Gly Asp
            405                 410                 415

Ser Ser Ala Ala Lys Ser Gly Leu Ala Leu Ile Thr Asp Gly Pro
            420                 425                 430

Gly Gly Ser Lys Arg Met Tyr Ala Gly Leu Lys Asn Ala Gly Glu Thr
            435                 440                 445

Trp Tyr Asp Ile Thr Gly Asn Arg Ser Asp Thr Val Lys Ile Gly Ser
        450                 455                 460

Asp Gly Trp Gly Glu Phe His Val Asn Asp Gly Ser Val Ser Ile Tyr
465                 470                 475                 480

Val Gln Lys

<210> SEQ ID NO 15
<211> LENGTH: 483
<212> TYPE: PRT
<213> ORGANISM: Bacillus stearothermophilus

<400> SEQUENCE: 15

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

```
Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
                340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
                420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg

<210> SEQ ID NO 16
<211> LENGTH: 485
<212> TYPE: PRT
<213> ORGANISM: Unknown
<220> FEATURE:
<223> OTHER INFORMATION: Synthetic construct

<400> SEQUENCE: 16

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
                20                  25                  30

Asn Leu Lys Asp Lys Gly Ile Ser Ala Val Trp Ile Pro Pro Ala Trp
            35                  40                  45

Lys Gly Ala Ser Gln Asn Asp Val Gly Tyr Gly Ala Tyr Asp Leu Tyr
50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Ser Gly Glu Tyr Thr Ile Glu Ala Trp Thr Lys Phe Asp
130                 135                 140

Phe Pro Gly Arg Gly Asn Thr His Ser Asn Phe Lys Trp Arg Trp Tyr
145                 150                 155                 160
```

His Phe Asp Gly Val Asp Trp Asp Gln Ser Arg Lys Leu Asn Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Asn Lys Thr Asn Trp Asn His Ser Val
        275                 280                 285

Phe Asp Val Pro Leu His Tyr Asn Leu Tyr Asn Ala Ser Lys Ser Gly
    290                 295                 300

Gly Asn Tyr Asp Met Arg Gln Ile Phe Asn Gly Thr Val Val Gln Arg
305                 310                 315                 320

His Pro Met His Ala Val Thr Phe Val Asp Asn His Asp Ser Gln Pro
                325                 330                 335

Glu Glu Ala Leu Glu Ser Phe Val Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Lys Ser
    370                 375                 380

Lys Ile Asp Pro Ile Leu Glu Ala Arg Gln Lys Tyr Ala Tyr Gly Arg
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Gly Asn Lys Trp Met Phe Val Gly Arg Asn Lys Ala Gly
        435                 440                 445

Gln Val Trp Thr Asp Ile Thr Gly Asn Arg Ala Gly Thr Val Thr Ile
    450                 455                 460

Asn Ala Asp Gly Trp Gly Asn Phe Ser Val Asn Gly Gly Ser Val Ser
465                 470                 475                 480

Ile Trp Val Asn Lys
                485

<210> SEQ ID NO 17
<211> LENGTH: 484
<212> TYPE: PRT
<213> ORGANISM: Unknown
<220> FEATURE:
<223> OTHER INFORMATION: Synthetic construct

<400> SEQUENCE: 17

Gly Ser Val Pro Val Asn Gly Thr Met Met Gln Tyr Phe Glu Trp Tyr
1               5                   10                  15

Leu Pro Asp Asp Gly Thr Leu Trp Thr Lys Val Ala Asn Asn Ala Gln
            20                  25                  30

-continued

Ser Leu Ala Asn Leu Gly Ile Thr Ala Leu Trp Leu Pro Ala Tyr
        35                  40                  45

Lys Gly Thr Ser Ser Asp Val Gly Tyr Gly Val Tyr Asp Leu Tyr
 50                  55                  60

Asp Leu Gly Glu Phe Asn Gln Lys Gly Thr Val Arg Thr Lys Tyr Gly
 65                  70                  75                  80

Thr Lys Thr Gln Tyr Ile Gln Ala Ile Gln Ala His Thr Ala Gly
                 85                  90                  95

Met Gln Val Tyr Ala Asp Val Val Phe Asn His Lys Ala Gly Ala Asp
                100                 105                 110

Gly Thr Glu Leu Val Asp Ala Val Glu Val Asn Pro Ser Asp Arg Asn
            115                 120                 125

Gln Glu Ile Ser Gly Thr Tyr Gln Ile Gln Ala Trp Thr Lys Phe Asp
        130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Gly Thr Gly Lys Ala Trp Asp Trp Glu Val Asp Thr
            180                 185                 190

Glu Asn Gly Asn Tyr Asp Tyr Leu Met Tyr Ala Asp Leu Asp Met Asp
        195                 200                 205

His Pro Glu Val Val Ser Glu Leu Lys Asn Trp Gly Lys Trp Tyr Val
210                 215                 220

Thr Thr Thr Asn Ile Asp Gly Phe Arg Leu Asp Ala Val Lys His Ile
225                 230                 235                 240

Lys Tyr Ser Phe Phe Pro Asp Trp Leu Ser Tyr Val Arg Thr Gln Thr
                245                 250                 255

Gln Lys Pro Leu Phe Ala Val Gly Glu Phe Trp Ser Tyr Asp Ile Asn
            260                 265                 270

Lys Leu His Asn Tyr Ile Thr Lys Thr Asn Gly Ser Met Ser Leu Phe
        275                 280                 285

Asp Ala Pro Leu His Asn Asn Phe Tyr Ile Ala Ser Lys Ser Gly Gly
290                 295                 300

Tyr Phe Asp Met Arg Thr Leu Leu Asn Asn Thr Leu Met Lys Asp Gln
305                 310                 315                 320

Pro Thr Leu Ser Val Thr Leu Val Asp Asn His Asp Thr Glu Pro Gly
                325                 330                 335

Gln Ser Leu Gln Ser Trp Val Glu Pro Trp Phe Lys Pro Leu Ala Tyr
            340                 345                 350

Ala Phe Ile Leu Thr Arg Gln Glu Gly Tyr Pro Cys Ile Phe Tyr Gly
        355                 360                 365

Asp Tyr Tyr Gly Ile Pro Lys Tyr Asn Ile Pro Ala Leu Lys Ser Lys
370                 375                 380

Leu Asp Pro Leu Leu Ile Ala Arg Arg Asp Tyr Ala Tyr Gly Thr Gln
385                 390                 395                 400

His Asp Tyr Ile Asp Asn Ala Asp Ile Ile Gly Trp Thr Arg Glu Gly
                405                 410                 415

Val Ala Glu Lys Ala Asn Ser Gly Leu Ala Ala Leu Ile Thr Asp Gly
            420                 425                 430

Pro Gly Gly Ser Lys Trp Met Tyr Val Gly Lys Gln His Ala Gly Lys
        435                 440                 445

Thr Phe Tyr Asp Leu Thr Gly Asn Arg Ser Asp Thr Val Thr Ile Asn
450                 455                 460

```
Ala Asp Gly Trp Gly Glu Phe Lys Val Asn Gly Gly Ser Val Ser Ile
465                 470                 475                 480

Trp Val Pro Lys

<210> SEQ ID NO 18
<211> LENGTH: 485
<212> TYPE: PRT
<213> ORGANISM: Unknown
<220> FEATURE:
<223> OTHER INFORMATION: Synthetic construct

<400> SEQUENCE: 18

Ala Asn Thr Ala Pro Ile Asn Glu Thr Met Met Gln Tyr Phe Glu Trp
1               5                   10                  15

Asp Leu Pro Asn Asp Gly Thr Leu Trp Thr Lys Val Lys Asn Glu Ala
            20                  25                  30

Ala Asn Leu Ser Ser Leu Gly Ile Thr Ala Leu Trp Leu Pro Pro Ala
        35                  40                  45

Tyr Lys Gly Thr Ser Gln Ser Asp Val Gly Tyr Gly Val Tyr Asp Leu
    50                  55                  60

Tyr Asp Leu Gly Glu Phe Asn Gln Lys Gly Thr Ile Arg Thr Lys Tyr
65                  70                  75                  80

Gly Thr Lys Thr Gln Tyr Ile Gln Ala Ile Gln Ala Ala Lys Ala Ala
                85                  90                  95

Gly Met Gln Val Tyr Ala Asp Val Val Phe Asn His Lys Ala Gly Ala
            100                 105                 110

Asp Gly Thr Glu Phe Val Asp Ala Val Glu Val Asp Pro Ser Asn Arg
        115                 120                 125

Asn Gln Glu Thr Ser Gly Thr Tyr Gln Ile Gln Ala Trp Thr Lys Phe
    130                 135                 140

Asp Phe Pro Gly Arg Gly Asn Thr Tyr Ser Ser Phe Lys Trp Arg Trp
145                 150                 155                 160

Tyr His Phe Asp Gly Thr Asp Trp Asp Glu Ser Arg Lys Leu Asn Arg
                165                 170                 175

Ile Tyr Lys Phe Arg Ser Thr Gly Lys Ala Trp Asp Trp Glu Val Asp
            180                 185                 190

Thr Glu Asn Gly Asn Tyr Asp Tyr Leu Met Phe Ala Asp Leu Asp Met
        195                 200                 205

Asp His Pro Glu Val Val Thr Glu Leu Lys Asn Trp Gly Thr Trp Tyr
    210                 215                 220

Val Asn Thr Thr Asn Ile Asp Gly Phe Arg Leu Asp Ala Val Lys His
225                 230                 235                 240

Ile Lys Tyr Ser Phe Phe Pro Asp Trp Leu Thr Tyr Val Arg Asn Gln
                245                 250                 255

Thr Gly Lys Asn Leu Phe Ala Val Gly Glu Phe Trp Ser Tyr Asp Val
            260                 265                 270

Asn Lys Leu His Asn Tyr Ile Thr Lys Thr Asn Gly Ser Met Ser Leu
        275                 280                 285

Phe Asp Ala Pro Leu His Asn Asn Phe Tyr Thr Ala Ser Lys Ser Ser
    290                 295                 300

Gly Tyr Phe Asp Met Arg Tyr Leu Leu Asn Asn Thr Leu Met Lys Asp
305                 310                 315                 320

Gln Pro Ser Leu Ala Val Thr Leu Val Asp Asn His Asp Thr Gln Pro
                325                 330                 335

Gly Gln Ser Leu Gln Ser Trp Val Glu Pro Trp Phe Lys Pro Leu Ala
```

```
                340             345             350
Tyr Ala Phe Ile Leu Thr Arg Gln Glu Gly Tyr Pro Cys Val Phe Tyr
            355                 360                 365
Gly Asp Tyr Tyr Gly Ile Pro Lys Tyr Asn Ile Pro Gly Leu Lys Ser
            370                 375                 380
Lys Ile Asp Pro Leu Leu Ile Ala Arg Arg Asp Tyr Ala Tyr Gly Thr
385                 390                 395                 400
Gln Arg Asp Tyr Ile Asp His Gln Asp Ile Ile Gly Trp Thr Arg Glu
                405                 410                 415
Gly Ile Asp Thr Lys Pro Asn Ser Gly Leu Ala Ala Leu Ile Thr Asp
                420                 425                 430
Gly Pro Gly Gly Ser Lys Trp Met Tyr Val Gly Lys Lys His Ala Gly
                435                 440                 445
Lys Val Phe Tyr Asp Leu Thr Gly Asn Arg Ser Asp Thr Val Thr Ile
                450                 455                 460
Asn Ala Asp Gly Trp Gly Glu Phe Lys Val Asn Gly Gly Ser Val Ser
465                 470                 475                 480
Ile Trp Val Ala Lys
                485

<210> SEQ ID NO 19
<211> LENGTH: 619
<212> TYPE: PRT
<213> ORGANISM: Bacillus flavothermus

<400> SEQUENCE: 19

Met Ser Leu Phe Lys Lys Ser Phe Pro Trp Ile Leu Ser Leu Leu Leu
1               5                   10                  15
Leu Phe Ser Phe Ile Ala Pro Phe Ser Ile Gln Thr Glu Lys Val Arg
                20                  25                  30
Ala Gly Ser Val Pro Val Asn Gly Thr Met Met Gln Tyr Phe Glu Trp
            35                  40                  45
Tyr Leu Pro Asp Asp Gly Thr Leu Trp Thr Lys Val Ala Asn Asn Ala
        50                  55                  60
Gln Ser Leu Ala Asn Leu Gly Ile Thr Ala Leu Trp Leu Pro Pro Ala
65                  70                  75                  80
Tyr Lys Gly Thr Ser Ser Ser Asp Val Gly Tyr Gly Val Tyr Asp Leu
                85                  90                  95
Tyr Asp Leu Gly Glu Phe Asn Gln Lys Gly Thr Val Arg Thr Lys Tyr
                100                 105                 110
Gly Thr Lys Thr Gln Tyr Ile Gln Ala Ile Gln Ala Ala His Thr Ala
            115                 120                 125
Gly Met Gln Val Tyr Ala Asp Val Val Phe Asn His Lys Ala Gly Ala
        130                 135                 140
Asp Gly Thr Glu Leu Val Asp Ala Val Glu Val Asn Pro Ser Asp Arg
145                 150                 155                 160
Asn Gln Glu Ile Ser Gly Thr Tyr Gln Ile Gln Ala Trp Thr Lys Phe
                165                 170                 175
Asp Phe Pro Gly Arg Gly Asn Thr Tyr Ser Ser Phe Lys Trp Arg Trp
                180                 185                 190
Tyr His Phe Asp Gly Thr Asp Trp Asp Glu Ser Arg Lys Leu Asn Arg
            195                 200                 205
Ile Tyr Lys Phe Arg Gly Thr Gly Lys Ala Trp Asp Trp Glu Val Asp
        210                 215                 220
Thr Glu Asn Gly Asn Tyr Asp Tyr Leu Met Tyr Ala Asp Leu Asp Met
```

```
                   225                 230                 235                 240

Asp His Pro Glu Val Val Ser Glu Leu Lys Asn Trp Gly Lys Trp Tyr
                        245                 250                 255

Val Thr Thr Thr Asn Ile Asp Gly Phe Arg Leu Asp Ala Val Lys His
                        260                 265                 270

Ile Lys Tyr Ser Phe Phe Pro Asp Trp Leu Ser Tyr Val Arg Thr Gln
                        275                 280                 285

Thr Gln Lys Pro Leu Phe Ala Val Gly Glu Phe Trp Ser Tyr Asp Ile
                290                 295                 300

Ser Lys Leu His Asn Tyr Ile Thr Lys Thr Asn Gly Ser Met Ser Leu
        305                 310                 315                 320

Phe Asp Ala Pro Leu His Asn Asn Phe Tyr Ile Ala Ser Lys Ser Gly
                        325                 330                 335

Gly Tyr Phe Asp Met Arg Thr Leu Leu Asn Asn Thr Leu Met Lys Asp
                        340                 345                 350

Gln Pro Thr Leu Ala Val Thr Leu Val Asp Asn His Asp Thr Glu Pro
                        355                 360                 365

Gly Gln Ser Leu Gln Ser Trp Val Glu Pro Trp Phe Lys Pro Leu Ala
                370                 375                 380

Tyr Ala Phe Ile Leu Thr Arg Gln Glu Gly Tyr Pro Cys Val Phe Tyr
        385                 390                 395                 400

Gly Asp Tyr Tyr Gly Ile Pro Lys Tyr Asn Ile Pro Ala Leu Lys Ser
                        405                 410                 415

Lys Leu Asp Pro Leu Leu Ile Ala Arg Arg Asp Tyr Ala Tyr Gly Thr
                        420                 425                 430

Gln His Asp Tyr Ile Asp Ser Ala Asp Ile Ile Gly Trp Thr Arg Glu
                        435                 440                 445

Gly Val Ala Glu Lys Ala Asn Ser Gly Leu Ala Ala Leu Ile Thr Asp
                450                 455                 460

Gly Pro Gly Gly Ser Lys Trp Met Tyr Val Gly Lys Gln His Ala Gly
        465                 470                 475                 480

Lys Thr Phe Tyr Asp Leu Thr Gly Asn Arg Ser Asp Thr Val Thr Ile
                        485                 490                 495

Asn Ala Asp Gly Trp Gly Glu Phe Lys Val Asn Gly Gly Ser Val Ser
                        500                 505                 510

Ile Trp Val Pro Lys Ile Ser Thr Ser Gln Ile Thr Phe Thr Val
                        515                 520                 525

Asn Asn Ala Thr Thr Val Trp Gly Gln Asn Val Tyr Val Val Gly Asn
        530                 535                 540

Ile Ser Gln Leu Gly Asn Trp Asp Pro Val His Ala Val Gln Met Thr
        545                 550                 555                 560

Pro Ser Ser Tyr Pro Thr Trp Thr Val Thr Ile Pro Leu Leu Gln Gly
                        565                 570                 575

Gln Asn Ile Gln Phe Lys Phe Ile Lys Lys Asp Ser Ala Gly Asn Val
                        580                 585                 590

Ile Trp Glu Asp Ile Ser Asn Arg Thr Tyr Thr Val Pro Thr Ala Ala
                        595                 600                 605

Ser Gly Ala Tyr Thr Ala Ser Trp Asn Val Pro
            610                 615

<210> SEQ ID NO 20
<211> LENGTH: 613
<212> TYPE: PRT
<213> ORGANISM: Bacillus species
```

<400> SEQUENCE: 20

Met Ser Tyr Leu Lys Lys Val Trp Leu Tyr Tyr Thr Ile Ile Ala Thr
1               5                   10                  15

Leu Ile Ile Ser Phe Phe Thr Pro Phe Ser Thr Ala Gln Ala Asn Thr
            20                  25                  30

Ala Pro Val Asn Gly Thr Met Met Gln Tyr Phe Glu Trp Asp Leu Pro
        35                  40                  45

Asn Asp Gly Thr Leu Trp Thr Lys Val Lys Asn Glu Ala Ser Ser Leu
50                  55                  60

Ser Ala Leu Gly Ile Thr Ala Leu Trp Leu Pro Pro Ala Tyr Lys Gly
65                  70                  75                  80

Thr Ser Gln Ala Asp Val Gly Tyr Gly Val Tyr Asp Leu Tyr Asp Leu
                85                  90                  95

Gly Glu Phe Asn Gln Lys Gly Thr Ile Arg Thr Lys Tyr Gly Thr Lys
            100                 105                 110

Thr Gln Tyr Leu Gln Ala Ile Gln Ala Ala Lys Ser Ala Gly Met Gln
        115                 120                 125

Val Tyr Ala Asp Val Val Phe Asn His Lys Ala Gly Ala Asp Ser Thr
130                 135                 140

Glu Trp Val Asp Ala Val Glu Val Asn Pro Ser Asn Arg Asn Gln Glu
145                 150                 155                 160

Thr Ser Gly Thr Tyr Gln Ile Gln Ala Trp Thr Lys Phe Asp Phe Pro
                165                 170                 175

Gly Arg Gly Asn Thr Tyr Ser Ser Phe Lys Trp Arg Trp Tyr His Phe
            180                 185                 190

Asp Gly Thr Asp Trp Asp Glu Ser Arg Lys Leu Asn Arg Ile Tyr Lys
        195                 200                 205

Phe Arg Gly Thr Gly Lys Ala Trp Asp Trp Glu Val Asp Thr Glu Asn
210                 215                 220

Gly Asn Tyr Asp Tyr Leu Met Phe Ala Asp Leu Asp Met Asp His Pro
225                 230                 235                 240

Glu Val Val Ala Glu Leu Lys Asn Trp Gly Lys Trp Tyr Val Asn Thr
                245                 250                 255

Thr Asn Val Asp Gly Phe Arg Leu Asp Ala Val Lys His Ile Lys Tyr
            260                 265                 270

Ser Phe Phe Pro Asp Trp Leu Ser Tyr Val Arg Asn Gln Thr Gly Lys
        275                 280                 285

Asn Leu Phe Ala Val Gly Glu Phe Trp Gly Tyr Asp Val Asn Lys Leu
290                 295                 300

His Asn Tyr Ile Thr Lys Thr Asn Gly Ala Met Ser Leu Phe Asp Ala
305                 310                 315                 320

Pro Leu His Asn Asn Phe Tyr Ile Ala Ser Lys Ser Gly Tyr Phe
                325                 330                 335

Asp Met Arg Tyr Leu Leu Asn Asn Thr Leu Met Lys Asp Gln Pro Ala
            340                 345                 350

Leu Ala Val Thr Leu Val Asp Asn His Asp Thr Gln Pro Gly Gln Ser
        355                 360                 365

Leu Gln Ser Trp Val Glu Pro Trp Phe Lys Pro Leu Ala Tyr Ala Phe
370                 375                 380

Ile Leu Thr Arg Gln Glu Gly Tyr Pro Cys Val Phe Tyr Gly Asp Tyr
385                 390                 395                 400

Tyr Gly Ile Pro Lys Tyr Asn Ile Pro Gly Leu Lys Ser Lys Ile Asp
                405                 410                 415

```
Pro Leu Leu Ile Ala Arg Arg Asp Tyr Ala Tyr Gly Thr Gln Arg Asp
            420                 425                 430

Tyr Ile Asp His Gln Asp Ile Ile Gly Trp Thr Arg Glu Gly Ile Asp
        435                 440                 445

Ala Lys Pro Asn Ser Gly Leu Ala Ala Leu Ile Thr Asp Gly Pro Gly
    450                 455                 460

Gly Ser Lys Trp Met Tyr Val Gly Lys Arg His Ala Gly Lys Val Phe
465                 470                 475                 480

Tyr Asp Leu Thr Gly Asn Arg Ser Asp Thr Val Thr Ile Asn Ala Asp
                485                 490                 495

Gly Trp Gly Glu Phe Lys Val Asn Gly Gly Ser Val Ser Ile Trp Val
            500                 505                 510

Ala Lys Thr Ser Asn Val Thr Phe Thr Val Asn Asn Ala Thr Thr Val
        515                 520                 525

Tyr Gly Gln Asn Val Tyr Val Val Gly Asn Ile Pro Glu Leu Gly Asn
    530                 535                 540

Trp Asn Ile Ala Asn Ala Ile Gln Met Thr Pro Ser Ser Tyr Pro Thr
545                 550                 555                 560

Trp Lys Thr Thr Val Ser Leu Pro Gln Gly Lys Ala Ile Glu Phe Lys
                565                 570                 575

Phe Ile Lys Lys Asp Ser Ala Gly Asn Val Ile Trp Glu Asn Ile Ala
            580                 585                 590

Asn Arg Thr Tyr Thr Val Pro Phe Ser Ser Thr Gly Ser Tyr Thr Ala
        595                 600                 605

Asn Trp Asn Val Pro
    610
```

<210> SEQ ID NO 21
<211> LENGTH: 619
<212> TYPE: PRT
<213> ORGANISM: Alkaliphilic bacillus

<400> SEQUENCE: 21

```
Met Ser Leu Phe Lys Lys Ile Phe Pro Trp Ile Leu Ser Leu Leu Leu
1               5                   10                  15

Leu Phe Ser Phe Ile Ala Pro Phe Ser Ile Gln Thr Glu Lys Val Arg
                20                  25                  30

Ala Gly Ser Val Pro Val Asn Gly Thr Met Met Gln Tyr Phe Glu Trp
            35                  40                  45

Tyr Leu Pro Asp Asp Gly Thr Leu Trp Thr Lys Val Ala Asn Asn Ala
        50                  55                  60

Gln Ser Leu Ala Asn Leu Gly Ile Thr Ala Leu Trp Leu Pro Pro Ala
65                  70                  75                  80

Tyr Lys Gly Thr Ser Ser Ser Asp Val Gly Tyr Gly Val Tyr Asp Leu
                85                  90                  95

Tyr Asp Leu Gly Glu Phe Asn Gln Lys Gly Thr Val Arg Thr Lys Tyr
            100                 105                 110

Gly Thr Lys Thr Gln Tyr Ile Gln Ala Ile Gln Ala Ala His Thr Ala
        115                 120                 125

Gly Met Gln Val Tyr Ala Asp Val Val Phe Asn His Lys Ala Gly Ala
    130                 135                 140

Asp Gly Thr Glu Leu Val Asp Ala Val Glu Val Asn Pro Ser Asp Arg
145                 150                 155                 160

Asn Gln Glu Ile Ser Gly Thr Tyr Gln Ile Gln Ala Trp Thr Lys Phe
                165                 170                 175
```

```
Asp Phe Pro Gly Arg Gly Asn Thr Tyr Ser Ser Phe Lys Trp Arg Trp
            180                 185                 190

Tyr His Phe Asp Gly Thr Asp Trp Asp Glu Ser Arg Lys Leu Asn Arg
        195                 200                 205

Ile Tyr Lys Phe Arg Gly Thr Gly Lys Ala Trp Asp Trp Glu Val Asp
    210                 215                 220

Thr Glu Asn Gly Asn Tyr Asp Tyr Leu Met Tyr Ala Asp Leu Asp Met
225                 230                 235                 240

Asp His Pro Glu Val Val Ser Glu Leu Lys Asn Trp Gly Lys Trp Tyr
                245                 250                 255

Val Ile Thr Thr Asn Ile Asp Gly Phe Arg Leu Asp Ala Val Lys His
            260                 265                 270

Ile Lys Tyr Ser Phe Phe Pro Asp Trp Leu Ser Tyr Leu Arg Thr Gln
        275                 280                 285

Thr Gln Lys Pro Leu Phe Ala Val Gly Glu Phe Trp Ser Tyr Asp Ile
    290                 295                 300

Asn Lys Leu His Asn Tyr Ile Thr Lys Thr Asn Gly Ser Met Ser Leu
305                 310                 315                 320

Phe Asp Ala Pro Leu His Asn Asn Phe Tyr Ile Ala Ser Lys Ser Gly
                325                 330                 335

Gly Tyr Phe Asp Met Arg Thr Leu Leu Asn Asn Thr Leu Met Lys Glu
            340                 345                 350

Gln Pro Thr Leu Ser Val Thr Leu Val Asp Asn His Asp Thr Glu Pro
        355                 360                 365

Gly Gln Ser Leu Gln Ser Trp Val Glu Pro Trp Phe Lys Pro Leu Ala
    370                 375                 380

Tyr Ala Phe Ile Leu Thr Arg Gln Glu Gly Tyr Pro Cys Val Phe Tyr
385                 390                 395                 400

Gly Asp Tyr Tyr Gly Ile Pro Lys Tyr Asn Ile Pro Ala Leu Lys Ser
                405                 410                 415

Lys Leu Asp Pro Leu Leu Ile Ala Arg Arg Asp Tyr Ala Tyr Gly Thr
            420                 425                 430

Gln His Asp Tyr Ile Asp Asn Ala Asp Ile Ile Gly Trp Thr Arg Glu
        435                 440                 445

Gly Val Ala Glu Lys Ala Asn Ser Gly Leu Ala Ala Leu Ile Thr Asp
    450                 455                 460

Gly Pro Gly Gly Ser Lys Trp Met Tyr Val Gly Lys Gln His Ala Gly
465                 470                 475                 480

Lys Thr Phe Tyr Asp Leu Thr Gly Asn Arg Ser Asp Thr Val Thr Ile
                485                 490                 495

Asn Ala Asp Gly Trp Gly Glu Phe Lys Val Asn Gly Gly Ser Val Ser
            500                 505                 510

Ile Trp Val Pro Lys Thr Ser Thr Ser Gln Ile Thr Phe Thr Val
        515                 520                 525

Asn Asn Ala Thr Thr Val Trp Gly Gln Asn Val Tyr Val Val Gly Asn
    530                 535                 540

Ile Ser Gln Leu Gly Asn Trp Asp Pro Val Asn Ala Val Gln Met Thr
545                 550                 555                 560

Pro Ser Ser Tyr Pro Thr Trp Val Val Thr Val Pro Leu Pro Gln Ser
                565                 570                 575

Gln Asn Ile Gln Phe Lys Phe Ile Lys Lys Asp Gly Ser Gly Asn Val
            580                 585                 590

Ile Trp Glu Asn Ile Ser Asn Arg Thr Tyr Thr Val Pro Thr Ala Ala
        595                 600                 605
```

```
Ser Gly Ala Tyr Thr Ala Asn Trp Asn Val Pro
    610             615
```

<210> SEQ ID NO 22
<211> LENGTH: 640
<212> TYPE: PRT
<213> ORGANISM: Aspergillus kawachii
<400> SEQUENCE: 22

```
Met Arg Val Ser Thr Ser Ser Ile Ala Leu Ala Val Ser Leu Phe Gly
1               5                   10                  15

Lys Leu Ala Leu Gly Leu Ser Ala Ala Glu Trp Arg Thr Gln Ser Ile
            20                  25                  30

Tyr Phe Leu Leu Thr Asp Arg Phe Gly Arg Thr Asp Asn Ser Thr Thr
        35                  40                  45

Ala Thr Cys Asn Thr Gly Asp Gln Ile Tyr Cys Gly Gly Ser Trp Gln
    50                  55                  60

Gly Ile Ile Asn His Leu Asp Tyr Ile Gln Gly Met Gly Phe Thr Ala
65              70                  75                  80

Ile Trp Ile Ser Pro Ile Thr Glu Gln Leu Pro Gln Asp Thr Ser Asp
                85                  90                  95

Gly Glu Ala Tyr His Gly Tyr Trp Gln Gln Lys Ile Tyr Tyr Val Asn
            100                 105                 110

Ser Asn Phe Gly Thr Ala Asp Asp Leu Lys Ser Leu Ser Asp Ala Leu
        115                 120                 125

His Ala Arg Gly Met Tyr Leu Met Val Asp Val Val Pro Asn His Met
    130                 135                 140

Gly Tyr Ala Gly Asn Gly Asn Asp Val Asp Tyr Ser Val Phe Asp Pro
145                 150                 155                 160

Phe Asp Ser Ser Ser Tyr Phe His Pro Tyr Cys Leu Ile Thr Asp Trp
                165                 170                 175

Asp Asn Leu Thr Met Val Gln Asp Cys Trp Glu Gly Asp Thr Ile Val
            180                 185                 190

Ser Leu Pro Asp Leu Asn Thr Thr Glu Thr Ala Val Arg Thr Ile Trp
        195                 200                 205

Tyr Asp Trp Val Ala Asp Leu Val Ser Asn Tyr Ser Val Asp Gly Leu
    210                 215                 220

Arg Ile Asp Ser Val Glu Glu Val Glu Pro Asp Phe Phe Pro Gly Tyr
225                 230                 235                 240

Gln Glu Ala Ala Gly Val Tyr Cys Val Gly Glu Val Asp Asn Gly Asn
                245                 250                 255

Pro Ala Leu Asp Cys Pro Tyr Gln Lys Tyr Leu Asp Gly Val Leu Asn
            260                 265                 270

Tyr Pro Ile Tyr Trp Gln Leu Leu Tyr Ala Phe Glu Ser Ser Ser Gly
        275                 280                 285

Ser Ile Ser Asn Leu Tyr Asn Met Ile Lys Ser Val Ala Ser Asp Cys
    290                 295                 300

Ser Asp Pro Thr Leu Leu Gly Asn Phe Ile Glu Asn His Asp Asn Pro
305                 310                 315                 320

Arg Phe Ala Ser Tyr Thr Ser Asp Tyr Ser Gln Ala Lys Asn Val Leu
                325                 330                 335

Ser Tyr Ile Phe Leu Ser Asp Gly Ile Pro Ile Val Tyr Ala Gly Glu
            340                 345                 350

Glu Gln His Tyr Ser Gly Gly Asp Val Pro Tyr Asn Arg Glu Ala Thr
        355                 360                 365
```

-continued

```
Trp Leu Ser Gly Tyr Asp Thr Ser Ala Glu Leu Tyr Thr Trp Ile Ala
        370                 375                 380

Thr Thr Asn Ala Ile Arg Lys Leu Ala Ile Ser Ala Asp Ser Asp Tyr
385                 390                 395                 400

Ile Thr Tyr Lys Asn Asp Pro Ile Tyr Thr Asp Ser Asn Thr Ile Ala
                405                 410                 415

Met Arg Lys Gly Thr Ser Gly Ser Gln Ile Ile Thr Val Leu Ser Asn
            420                 425                 430

Lys Gly Ser Ser Gly Ser Ser Tyr Thr Leu Thr Leu Ser Gly Ser Gly
        435                 440                 445

Tyr Thr Ser Gly Thr Lys Leu Ile Glu Ala Tyr Thr Cys Thr Ser Val
    450                 455                 460

Thr Val Asp Ser Asn Gly Asp Ile Pro Val Pro Met Ala Ser Gly Leu
465                 470                 475                 480

Pro Arg Val Leu Leu Pro Ala Ser Val Val Asp Ser Ser Ser Leu Cys
                485                 490                 495

Gly Gly Ser Gly Asn Thr Thr Thr Thr Thr Ala Ala Thr Ser Thr
            500                 505                 510

Ser Lys Ala Thr Thr Ser Ser Ser Ser Ser Ala Ala Ala Thr Thr
        515                 520                 525

Ser Ser Ser Cys Thr Ala Thr Ser Thr Thr Leu Pro Ile Thr Phe Glu
530                 535                 540

Glu Leu Val Thr Thr Thr Tyr Gly Glu Glu Val Tyr Leu Ser Gly Ser
545                 550                 555                 560

Ile Ser Gln Leu Gly Glu Trp His Thr Ser Asp Ala Val Lys Leu Ser
            565                 570                 575

Ala Asp Asp Tyr Thr Ser Ser Asn Pro Glu Trp Ser Val Thr Val Ser
            580                 585                 590

Leu Pro Val Gly Thr Thr Phe Glu Tyr Lys Phe Ile Lys Val Asp Glu
        595                 600                 605

Gly Gly Ser Val Thr Trp Glu Ser Asp Pro Asn Arg Glu Tyr Thr Val
    610                 615                 620

Pro Glu Cys Gly Ser Gly Ser Gly Glu Thr Val Val Asp Thr Trp Arg
625                 630                 635                 640
```